United States Patent
Reich et al.

(10) Patent No.: US 6,369,226 B1
(45) Date of Patent: Apr. 9, 2002

(54) SUBSTITUTED BENZAMIDE INHIBITORS OF RHINOVIRUS 3C PROTEASE

(75) Inventors: Siegfried Heinz Reich, Solana Beach; Susan Elizabeth Kephart, La Jolla; Michael Brennan Wallace; Theodore Otto Johnson, Jr., both of San Diego, all of CA (US)

(73) Assignee: Agouron Pharmaceuticals, Inc.

( * ) Notice: Subject to any disclaimer, the term of this patent is extended or adjusted under 35 U.S.C. 154(b) by 0 days.

(21) Appl. No.: 09/597,148

(22) Filed: Jun. 20, 2000

Related U.S. Application Data
(60) Provisional application No. 60/140,469, filed on Jun. 21, 1999.

(51) Int. Cl.$^7$ ................... C07D 211/74; C07D 233/28; C07C 229/00; C07C 233/00; C07B 55/00
(52) U.S. Cl. .................. 544/295; 544/393; 544/360; 544/389; 560/37; 564/169; 558/401; 546/269.4; 546/329
(58) Field of Search .................. 544/295, 393, 544/360, 389; 560/37; 564/169; 558/401; 546/269.4, 329

(56) References Cited

U.S. PATENT DOCUMENTS

| | | | |
|---|---|---|---|
| 4,963,578 A | * 10/1990 | Baker et al. | 514/381 |
| 5,856,530 A | 1/1999 | Weber et al. | 549/478 |
| 5,962,487 A | 10/1999 | Webber et al. | 514/378 |
| 6,020,371 A | 2/2000 | Dragovich et al. | 514/514 |

OTHER PUBLICATIONS

CAS printout for Yoon et al., Jan. 1993.*
G. Bertolini et al, *J. Med. Chem.* 40, 2011–2016 (1997).
N. Bodor, *"Advances in Drug Research"* 13, 224–331 (1984).
H. Bundgard *"Design of Prodrugs"* (Elsievier, New York 1985).
H. Bundgaard *"Design and Application of Prodrugs"* *"Design and Application of Prodrugs, Drugs Desugn and Development"* Chapt. 5, 113–139, Krugsgarrd–Larsen et al, Eds., (Harwood Academic Publishers, 1991).
G. Friis et al. *"Design and Application of Prodrugs"* in *"Design and Application of Prodrugs, Drug and Design and Development"* Chapt. 13, 351–385, Krugsgarrd–Larsen et al, Eds., (Harwood Academic Publishers, 1991).
A. Prox et al., *Xenobiotica*, 1973, vol. 3, No. 2, 103–112.
M. Spraul et al, *"Journal of Pharmaceutical and Bio–Medical Analysis"* 1992, vol. 10, No. 8, 601–605.
Kadam, S., et al., "Citrinin Hydrate and Radicinin: Human Rhinovirus 3C–Protease Inhibitors Discovered in a Target–Directed Microbial Screen", Antibiotics (1994) vol. 47, No. 7, pp. 836–839.

Singh, S.B., et al., "Structure and Stereochemistry of Thysanone: A Novel Human Rhinovirus 3C–Protease Inhibitor From Thysanophora Penicilloides", Tetrahedron Lett. (1991) vol. 32, No. 39, pp. 5279–5282.
Jungheim, L.N., et al., "Inhibition of Human Rhinovirus 3C Protease by Homophthalimides", Bioorg. Med. Chem. Lett. (1997), vol. 7, No. 12, pp. 1589–1594.
Kong, J., et al., "Synthesis and Evaluation of Peptidyl Michael Acceptors that Inactivate Human Rhinovirus 3C Protease and Inhibit Virus Replication", J. Med. Chem. (1998) vol. 41, No. 14, pp. 2579–2587.
Couch, R.B., "Rhinoviruses", *Virology*; Fields, B.N., Knipe, D.M., Eds.; Raven Press: New York (1990), vol. 1, Chapter 22, pp. 607–629.
McKinlay, M.A., et al., "Treatment of the Picornavirus Common Cold by Inhibitors of Viral Uncoating and Attachment", Annu. Rev. Microbio. (1992), vol. 46, pp. 635–654.
Phillpotts, R.J., et al., "Rhinovirus Colds", Br. Med. Bull. (1985) vol. 41, No. 4, pp. 386–390.
Gwaltney, J.M., "Rhinoviruses," *Viral Infections of Humans*, Evans, A.S., Ed.; Plunem Publishing Corp.: New York (1982) Chapter 20, pp. 491–517.
Lee, W., et al., Complete Sequence of the RNA Genome of Human Rhinovirus 16, a Clinically Useful Common Cold Virus Belonging to the ICAM–1 Receptor Group, *Virus Genes* (1995) vol. 9, No. 2, pp. 177–181.
Orr, D.C., et al., "Hydrolysis of a Series of Synthetic Peptide Substrates by the Human Rhinovirus 14 3C Protease, Cloned and Express in Escherichia coli", J. Gen. Virol. (1989). vol. 70, pp. 2931–2942.
Cordingley, M.G., et al., "Cleavage of Smal Peptides in Vitro by Human Rhinovirus 14 3C Protease Expressed in Echerichia coli", J. Virol. (1989) vol. 63, No. 12, pp. 5037–5045.
Matthews, D.A., et al., "Structure of Human Rhinovirus 3C Protease Reveals a Trypsin–like Polypeptide Fold, RNA–Binding Site, and Means for Cleaving Precursor Polyprotein", *Cell* (1994) vol. 77, pp. 761–771.
Bazan, J.F., et al., "Viral Cysteine Protease are Homologous to the Trypsin–Like Family of Serine Proteases: Structural and Functional Implications", Proc. Natl. Acad Sci. USA (1988) vol. 85, No. 21, pp. 7872–7876.
Gorbalenya, A.E., et al., "Poliovirus–encoded Proteinase 3C: A Possible Evolutionary Link Between Cellular Serine and Cysteine Proteinase Families", FEBS Lett. (1986) vol. 194, No. 2, pp. 253–257.
Allaire, M., et al., "Picornaviral 3C Cysteine Proteinases Have a Fold Similar to Chymotrypsin–like Serine Proteinases", Nature (1994) vol. 369, No. 6475, pp. 72–76.

(List continued on next page.)

*Primary Examiner*—Richard L. Raymond
*Assistant Examiner*—Hong Liu

(57) ABSTRACT

Nonpeptide benzamide-containing inhibitors of human rhinovirus (HRV) 3C protease are described.

4 Claims, No Drawings

OTHER PUBLICATIONS

Ivanoff, L.A., et al., "Expression and site–specific mutagenesis of the poliovirus3C protease in *Escherichia coli*", Proc. Nat. Acad. Sci. U.S.A. (1986) vol. 83, No. 15, pp. 5392–5396.

Hammerle, T., et al., "Site–directed Mutagenesis of the Putative Catalytic Triad of Poliovirus 3C Proteinase", J. Biol. Chem. (1991) vol. 266, No. 9, pp. 5412–5416.

Webber, S.E., et al., "Design, Synthesis, and Evaluation of Nonpeptidic Inhibitors of Human Rhinovirus 3C Protease", J. Med. Chem. (1996) vol. 39, No. 26, pp. 5072–5082.

Webber, S.E., et al., "Tripeptide Aldehyde Inhibitors of Human Rhinovirus 3C Protease: Design, Synthesis, Biological Evaluation, and Cocrystal Structure Solution of P1 Gluamine Isosteric Replacements", J. Med. Chem. (1998) vol. 41, No. 15, pp. 2786–2805.

Dragovich, P.S., et al., "Structure–Based Design, Synthesis, and Biological Evaluation of Irreversible Human Rhinovirus 3C Protease Inhibitors. 1. Michael Acceptor Structure–Activity Studies", J. Med. Chem. (1998) vol. 41, No. 15, pp. 2806–2818.

Dragovich, P.S., et al., "Structure–Based Design, Synthesis, and Biological Evaluation of Irreversible Human Rhinovirus 3C Protease Inhibitors. 2. Peptide Structure–Activity Studies", J. Med. Chem. (1998). vol. 41, No. 15, pp. 2819–2834.

Kaldor, S.W., et al., "Glutamine–derived Aldehydes for the Inhibition of Human Rhinovirus 3C Protease", Bioorg. Med. Chem. Lett. (1995) vol. 5, No. 17, pp. 2021–2026.

Shepherd, T.A.,et al., "Small Peptidic Aldehyde Inhibitors of Human Rhinovirus 3C Protease", Bioorg. Med. Chem. Lett. (1996) vol. 6, No. 23, pp. 2893–2896.

Malcolm, B.A. et al., "Peptide Aldehyde Inhibitors of Hepatitis A Virus 3C Proteinase", Biochem. (1995) vol. 34, No. 25, pp. 8172–8179.

Sham, H. et al., "Potent Inhibitor of the Human Rhinovirus (HRV) 3C Protease Containing a Backbone Modified Glutamine", J. Chem. Soc. Perkin Trans. 1 (1995) pp. 1081–1082.

Brill, G.M., et al., "Novel Triterpene Sulfates From *Fusarium Compactum* Using a Rhinovirus 3C Protease Inhibitor Screen", J. Antibiotics (1996) vol. 49, No. 6, pp. 541–546.

Skiles, J. W., et al. "Spiro–Indolinone Beta–Lactams, Inhibitors of Poliovirus and Rhinovirus 3C–Proteinases", Tetrahedron Lett. (1990) vol. 31, No. 50, pp. 7277–7280.

Gwaltney, J.M., "The Common Cold", in Principles and Practices of Infectious Diseases, Second Edition, Mandell, G.L. et al., New York (1985) Chapter 38, pp. 351–355.

Krausslich, H.G. et al., "Viral Proteinases", Ann. Rev. Biochem. (1988) vol. 57, pp. 701–754.

Callahan, P.L. et al., "Molecular Cloning and Complete Sequence Determination of RNA Genome of Human Rhinovirus Type 14", Proc. Natl. Acad. Sci. USA (1985) vol. 82, No. 3, pp. 732–736.

Stanway, G., et al., "The Complete Nucleotide Sequence of the Common Cold Virus: Human Rhinovirus 14", Nucleic Acids Res. (1984) vol. 12, No. 20, pp. 7859–7875.

Mohamadi, F., et al., "MacroModel —An Intergrated Software System for Modeling Organic and Bioorganic Molecules Using Molecular Mechnics", *J. Comput. Chem.* (1990) vol. 11, No. 4, pp. 440–467.

Gehlhaar, D.K., et al., "Molecular Recognition of the Inhibitor AG–1343 by HIV–1 Protease: conformationally flexible docking by evolutionary programming", *Chemistry and Biology* (1995) vol. 2, No. 5, pp. 317–324.

Gehlhaar, D.K., et al., "Reduced Dimensionally in Ligand- –Protein Structure Prediction: Covalent Inhibitors of Serine Proteases and Design of Site–Directed Combinatoral Libraries", ACS Symposium Series on Rational Drug Design, Chapter 19, American Chemical Society (1998) pp. 292–311.

Molander, G.A., et al., "Reduction of 2–Acylaziridines by Samarium(II) Iodide. An Efficient and Regioselective Route to β–Amino Carbonyl Compounds", *Tetrahedron* (1997), vol. 53, No. 26, pp. 8887–8912.

Sieber, P., et al., "Protection of Carboxamide Functions by the Trityl Residue. Application to Peptide Synthesis", *Tetrahedron Lett.* (1991) vol. 32, No. 6, pp. 739–742.

Dondoni, A., et al., "Addition of 2–Lithiofuran to Chiral α–Alkoxy Nitrones; a Stereoselective Approach to α–Epimeric β–Alkoxy–α–amino Acids", *Synthesis* (1994) No. 12, pp. 1450–1456.

Kean, K.M., et al., "Analysis of Putative Active Site Residues of the Poliovirus 3C Protease", Virology (1991) vol. 181, No. 2, pp. 609–619.

\* cited by examiner

SUBSTITUTED BENZAMIDE INHIBITORS OF RHINOVIRUS 3C PROTEASE

RELATED APPLICATION DATA

This application claims the benefit of U.S. Provisional Application No. 60/140,469, filed Jun. 21, 1999.

FIELD OF THE INVENTION

The invention is directed to certain substituted benzamide compounds that are useful as inhibitors of picornaviruses such as human rhinoviruses (HRV). The invention is also directed to pharmaceutical compositions containing such compounds, as well as methods of treating HRV infection or the common cold by administering effective amounts of such compounds.

BACKGROUND OF THE INVENTION

HRVs, which are the primary cause of the common cold in man, belong to the picornavirus family. (Couch, R. B. Rhinoviruses. In *Virology*; Fields, B. N., Knipe, D. M., Eds.; Raven Press: New York, 1990; Volume 1, Chapter 22, pp 607–629; See McKinlay, M. A.; Pevear, D. C.; Rossman, M. G. Treatment of the Picornavirus Common Cold by Inhibitors of Viral Uncoating and Attachment. *Annu. Rev. Microbiol.* 1992, 46, 635–654, and references cited therein; Phillpotts, R. J., Tyrell, D. A. J. Rhinovirus Colds. *Br. Med. Bull.* 1985, 41, 386–390; Gwaltney, J. M. Rhinoviruses. In *Viral Infections of Humans*, Evans, A. S., Ed.; Plunem Publishing Corp.: New York, 1982; Chapter 20, pp 491–517; Gwaltney, J. M. The Common Cold. In *Principles and Practices of Infectious Diseases*, Mandell, G. L., Douglas, R. G., Bennett, J. E., Eds.; John Wiley & Sons: New York, 1985; Chapter 38, pp 351–355.) Picornaviruses, such as HRV, have a single positive-stranded RNA genome, (See Kräusslich, H. -G., Wimmer, E. Viral Proteinases. *Annu. Rev. Biochem.* 1988, 57, 701–754, and references cited therein; Callahan, P. L.; Mizutani, S.; Colonno, R. J. Molecular Cloning and Complete Sequence Determination of the RNA Genome of Human Rhinovirus Type 14. *Proc. Natl. Acad. Sci. USA* 1985, 82, 732–736; Stanway, G., Hughes, P. J., Mountford, R. C.; Minor, P. D., Almond, J. W. The complete nucleotide sequence of the common cold virus: human rhinovirus 14. *Nucleic Acids Res.* 1984, 12, 7859–7875; Lee, W. -M., Wang, W., Rueckart, R. R. Complete sequence of the RNA genome of human rhinovirus 16, a clinically useful common cold virus belonging to the ICAM-1 receptor group. *Virus Genes* 1995, 9, 177–181.), which is translated into a polyprotein of over 2000 amino acids. The 2A and 3C protease (3CP) process this polyprotein into its functional viral proteins in HRV. (Orr, D. C., Long, A. C., Kay, J., Dunn, B. M., Cameron, J. M. Hydrolysis of a Series of Synthetic Peptide Substrates by the Human Rhinovirus 14 3C Protease, Cloned and Express in *Escherichia coli*. *J. Gen. Virol.* 1989, 70, 2931–2942. Cordingly, M. G.; Register, R. B.; Callahan, P. L., Garsky, V. M., Colonno, R. J. Cleavage of Small Peptides In Vitro by Human Rhinovirus 14 3C Protease Expressed in *Escherichia coli*. *J. Virol.* 1989, 63, 5037–5045.) The consensus cleavage site for the 3CP in the viral polyprotein is between glutamine (P1) and glycine (P1') residues. While the 3CP is a cysteine protease, its tertiary structure is reminiscent of trypsin-like serine proteases. (Matthews, D. A., Smith, W. A., Ferre, R. A., Condon, B., Budahazi, G., Sisson, W., Villafranca, J. E., Janson, C. A., McElroy, H. E., Gribskov, C. L., Worland, S. Structure of Human Rhinovirus 3C Protease Reveals a Trypsin-like Polypeptide Fold, RNA-Binding Site, and Means for Cleaving Precursor Polyprotein. *Cell* 1994, 77, 761–771. Bazan, J. F., Fletterick, R. J. Viral Cysteine Proteases are Homologous to the Trypsin-like Family of Serine Proteases: Structural and Functional Implications. *Proc. Natl. Acad. Sci. USA* 1988, 85, 7872–7876; Gorbalenya, A. E., Blinov, V. M., Donchenko, A. P. Poliovirus-encoded Proteinase 3C: A Possible Evolutionary Link Between Cellular Serine and Cysteine Proteinase Families. *FEBS Lett.* 1986, 194, 253–257; Allaire, M., Chernala, M. M., Malcolm, B. A., James, M. N. G. Picornaviral 3C cysteine proteinases have a fold similar to chymotrypsin-like serine proteinases. *Nature* 1994, 369, 72–76.) The requirement for proteolytic processing of the viral polyprotein, supported by mutagenesis of the active site residues, (Ivanoff, L. A., Towatari, T., Ray, J., Korant, B. D., Petteway, S. R., Jr. *Proc. Nat. Acad. Sci. U.S.A.* 1986 83, 5392–5396; Hammerle, T., Hellen, C. U. T., Wimmer, E. *J. Biol. Chem.* 1991 266 5412–541; Kean, K. M., Teterina, N. L., Marc, D., Girard, M. *Virology* 1991 181 609–619) makes the 3CP a viable target for antirhinoviral therapy.

Solution of the HRV 3CP crystal structure has facilitated the design of a number of 3CP inhibitors, which have been previously reported (Webber, S. E., Tikhe, J., Worland, S. T., Fuhrman, S. A., Hendrickson, T. F., Matthews, D. A., Love, R. A., Patick, A. K., Meador, J. W., Ferre, R. A., Brown, E. L., DeLisle, D. M., Ford, C. E., Binford, S. L. Design, Synthesis, and Evaluation of Nonpeptidic Inhibitors of Human Rhinovirus 3C Protease. *J. Med. Chem.* 1996, 39, 5072–5082; Webber, S. E., Okano, K., Little, T., Reich, S. H., Xin, Y., Fuhrman, S. A., Matthews, D. A., Love, R. A., Hendrickson, T. F., Patick, A. K., Meador, J. W., Ferre, R. A., Brown, E. L., Ford, C. E., Binford, S. L., Worland, S. T. Tripeptide Aldehyde Inhibitors of Human Rhinovirus 3C Protease: Design, Synthesis, Biological Evaluation, and Cocrystal Structure Solution of P1 Glutamine Isosteric Replacements *J. Med. Chem.* 1998, 41, 2786–2805; Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L., Harr, J.E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806; Dragovich, P. S., Webber, S. E, Babine, R. E., Fuhrman, S. A., Patick, A. K., Matthews, D. A., Reich, S. H., Marakovits, J. T., Prins, T. J., Zhou, R., Tikhe, J., Littlefield, E. S., Bleckman, T. M., Wallace, M. W., Little, T. L., Ford, C. E., Wallace, M. B., Meador, III, J. W., Ferre, R., Brown, E. L., Binford, S. L, DeLisle, D. M. and Worland, S. T. Structure-Based Design, Synthesis, and Biological Evaluation of Irreversible Human Rhinovirus 3C Protease Inhibitors. 2. Peptide Structure-Activity Studies. *J. Med. Chem.* 1998, 41, 2819; Kaldor, S. W., Hammond, M., Dressman, B. A., Labus, J. M., Chadwell, F. W., Kline, A. D., Heinz, B. A. Glutamine-derived Aldehydes for the Inhibition of Human Rhinovirus 3C Protease. *Bioorg. Med. Chem. Lett.* 1995, 5, 2021–2026; Shepherd, T. A., Cox, G. A., McKinney, E., Tang, J., Wakulchik, M., Zimmerman, R. E., Villarreal, E. C. Small Peptidic Aldehyde Inhibitors of Human Rhinovirus 3C Protease. *Bioorg. Med. Chem. Lett.* 1996, 6, 2893–2896; Malcolm, B. A., Lowe, C., Shechosky, S., McKay, R. T., Yang, C. C., Shah, V. J., Simon, R. J., Vederas, J. C., Santi, D. V. Peptide Aldehyde Inhibitors of Hepatitis A Virus 3C Proteinase. *Biochem.* 1995, 34, 8172–8179. Sham, H. L., Rosenbrook, W., Kati, W., Betebenner, D. A., Wideburg, N.

E., Saldivar, A., Plattner, J. J., Norbeck, D. W. Potent inhibitor of the human rhinovirus (HRV) 3C protease containing a backbone modified glutamine. *J. Chem. Soc. Perkin Trans.* 1 1995, 1081–1082; Brill, G. M., Kati, W. M., Montgomery, D., Karwowski, J. P., Humphrey, P. E., Jackson, M., Clement J. J., Kadam, S., Chen, R. H., McAlpine, J. B. Novel Triterpene Sulfates from *Fusarium compactum* Using a Rhinovirus 3C Protease Inhibitor Screen. *J. Antibiotics* 1996, 49, 541–546; Skiles, J. W., McNeil, D. Spiro Indolinone Beta-lactams, Inhibitors of Poliovirus and Rhinovirus 3C-Proteinases. *Tetrahedron Lett.* 1990, 31, 7277–7280; Kadam, S., Poddig, J., Humphrey, P., Karwowski, J., Jackson, M., Tennent, S., Fung, L., Hochlowski, J., Rasmussen, R., McAlpine, J. Citrinin Hydrate and Radicinin: Human Rhinovirus 3C-Protease Inhibitors Discovered in a Target-directed Microbial Screen. *J. Antibiotics* 1994, 47, 836–839; Singh, S. B., Cordingley, M. G., Ball, R. G., Smith, J. L., Dombrowski, A. W., Goetz, M. A. Structure and Stereochemistry of Thysanone: A Novel Human Rhinovirus 3C-Protease Inhibitor from Thysanophora penicilloides. *Tetrahedron Lett.* 1991, 32, 5279–5282; Jungheim, L. N., Cohen, J. D., Johnson, R. B., Villarreal, E. C., Wakulchik, M., Loncharich, R. J., Wang, Q. M. Inhibition of Human Rhinovirus 3C Protease by Homophthalimides. *Bioorg. Med. Chem. Lett.* 1997, 7, 1589–1594; Kong, J., Venkatraman, S., Furness, K., Nimkar, S., Shepard, T., Wang, Q., Aube', J., Hanzlik, R. P. Synthesis and Evaluation of Peptidyl Michael Acceptors That Inactivate Human Rhinovirus 3C Protease and Inhibit Virus Replication *J. Med. Chem.* 1998 41 2579–2587.) There is still a desire, however, to discover nonpeptide, low molecular weight inhibitor of 3CP with potent antirhinoviral activity.

SUMMARY OF THE INVENTION

Accordingly, an object of the invention is to discover small-molecule, nonpeptide inhibitors of HRV 3CP (RVP). An additional object is to discover irreversible inhibitors of RVP that are orally available.

Other objects and advantages of the invention, which will become apparent from the detailed description that follows, have been achieved through the discovery of benzamide-containing compounds such as those of the following general formula:

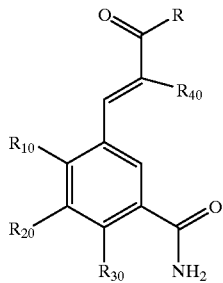

wherein:
$R_{10}$, $R_{20}$, and $R_{30}$ are each independently hydrogen, hydroxy, or halogen, or an unsubstituted or substituted alkyl, O-alkyl, aryl, O-aryl, heteroaryl, O-heteroaryl, alkoxy, aryloxy, or heteroaryloxy group;
$R_{40}$ is hydrogen or an unsubstituted or substituted alkyl or aryl group; and
R is an unsubstituted or substituted alkyl, aryl, heteroaryl, O-alkyl, O-aryl, or O-heteroaryl group.

Such compounds, as well as their pharmaceutically acceptable salts, solvates, prodrugs, and pharmaceutically active metabolites, are useful agents for pharmaceutical indications mediated by inhibition of RVP, such as for cold treatments.

DETAILED DESCRIPTION OF INVENTION

The RVP-inhibiting agents of the invention include the specific benzamide-containing compounds exemplified below as well as prodrugs, pharmaceutically active metabolites, solvents, and pharmaceutically acceptable salts thereof.

A "prodrug" is intended to mean a compound that is converted under physiological conditions or by solvolysis or metabolically to a specified compound that is pharmaceutically active.

A "pharmaceutically active metabolite" is intended to mean a pharmacologically active product produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, (-hydroxybutyrates, glycollates, tartrates, methanesulfonates, propanesulfonates, naphthalene-1-sulfonates, naphthalene-2-sulfonates, and mandelates.

If an inventive compound is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention and specified formulas.

The inventive compounds may exist as single stereoisomers, racemates, and/or mixtures of enantiomers and/or diastereomers. All such single stereoisomers, racemates, and mixtures thereof are intended to be within the broad scope of the present invention. Preferably, however, the inventive compounds are used in optically pure form.

As generally understood by those skilled in the art, an optically pure compound is one that is enantiomerically pure. As used herein, the term "optically pure" is intended to mean a compound comprising at least a sufficient activity. Preferably, an amount of a single enantiomer is provided to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

The present invention is also directed to a method of inhibiting picornaviral 3C protease activity, comprising contacting the protease with an effective amount of an inventive compound or a pharmaceutically acceptable salt, prodrug, pharmaceutically active metabolite, or solvate thereof. For example, picornaviral 3C protease activity may be inhibited in mammalian tissue by administering a compound shown in the tables below or a pharmaceutically acceptable salt, prodrug, pharmaceutically active metabolite, or solvate thereof. More preferably, the present method is directed at inhibiting rhinoviral protease activity.

"Treating" or "treatment" is intended to mean at least the mitigation of a disease condition in a mammal, such as a human, that is alleviated by the inhibition of the activity of one or more picornaviral 3C proteases, such as human rhinoviruses, human poliovirus, human coxsackieviruses, encephalomyocarditis viruses, meningitis virus, and hepatitis A virus, and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The activity of the inventive compounds as inhibitors of picornaviral 3C protease activity may be measured by any of the suitable methods known to those skilled in the art, including in vivo and in vitro assays. An example of a suitable assay for activity measurements is an antiviral H1-HeLa cell culture assay.

Administration of the compounds of the formula I and their pharmaceutically acceptable prodrugs, salts, active metabolites, and solvates may be performed according to any of the accepted modes of administration available to those skilled in the art. Illustrative examples of suitable modes of administration include oral, nasal, parenteral, topical, transdermal, and rectal. Intranasal delivery is especially preferred.

An inventive compound or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use. In preferred embodiments, the inventive pharmaceutical compositions are delivered intranasally in the form of suspensions.

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension.

A dose of the pharmaceutical composition contains at least a therapeutically effective amount of the active ingredient (i.e., an agent of the invention) and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including topically, for example, as an ointment or cream; orally; rectally, for example, as a suppository; parenterally by injection; or continuously by intravaginal, intranasal, intrabronchial, intraaural, or intraocular infusion.

A "therapeutically effective amount" is intended to mean the amount of an inventive compound that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

By way of illustration, a formulation for nasal delivery of the inventive compounds for treatment of rhinoviral infections can be prepared as follows, where all percentages are weight/weight and the suspension is prepared in purified water. A compound is micronized to a reduced particle size such that $D_{90}<10$ μm. A suspension is prepared to contain a final concentration of from about 0.01% to about 2% of the active compound, preferably about from 0.2% to 2%. An appropriate preservative selected from those known in the art may be included, for example, benzalkonium chloride/EDTA, in appropriate final-concentration ranges, e.g., about 0.02%/0.01%. A suspending agent, such as mixture of microcrystalline cellulose (final concentration of about 1%–1.5%, preferably about 1.2%) and sodium carboxymethylcellulose cellulose (final concentration of about 0.1%–0.2%, preferably about 0.13%) may be included. A surfactant such as polysorbate 80 may be included in a final concentration of about from 0.05% to 0.2%, preferably about 0.1%. A tonicity modifier such as dextrose may be included to give a final concentration of about from 4% to 6%, preferably about 5%. The pH of the final solution is adjusted as appropriate to a physiological range, e.g., 4–6, using non-toxic acid and/or base, such as HCl and/or NaOH.

Preferred compounds of the invention and their syntheses and testing are described in the following detailed examples.

Analytical Methods

Melting points (mp) were determined on a Mel-Temp apparatus and are uncorrected. The structures of the compounds were confirmed by proton magnetic resonance spectroscopy, infrared spectroscopy, and either elemental microanalysis or by mass spectrometry. Proton magnetic resonance spectra were determined using a General Electric QE-300 spectrometer operating at a field strength of 300 MHz. Chemical shifts are reported in parts per million (ppm) and by setting the references such that, in $CDCl_3$, the $CHCl_3$ peak is at 7.26 ppm, and in DMSO-$D_6$ the DMSO peak is at 2.49 ppm, and in acetone $D_6$ the acetone peak is at 2.04 ppm. Standard and peak multiplicities are designated as follows: s, singlet; d, doublet; dd, doublet of doublets; t, triplet; brs, broad singlet; brd, broad doublet; br, broad signal; and m, multiplet. Mass spectra were determined at Scripps Research Institute, San Diego, Calif., Mass Spectrometric Facilities. Infrared absorption spectra were taken on a Perkin-Elmer 457 spectrometer or a MIDAK high resolution FT IR and values are reported in $cm^{-1}$. Elemental microanalyses were performed by Atlantic Microlabs Inc., Norcross, Ga., and gave results for the elements stated within ±0.4% of the theoretical values.

N,N-Dimethylformamide and N,N-dimethylacetamide were used as obtained from Aldrich. Tetrahydrofuran (THF) was distilled from sodium benzophenone ketyl or $CaH_2$ under nitrogen. Flash chromatography was performed using silica gel 60 (Merck Art 9385), unless stated otherwise. Thin layer chromatographs (TLC) were performed on precoated sheets of silica 60 F254 (Merck Art 5719). Abbreviations: NMO=4-methylmorpholine N-oxide; TPAP=tetrapropylammonium perruthenate; TBAF=tetrabutylammonium fluoride; HATU=O-(7-Azabenzotriazol-1-yl)-N,N,N',N'-tetramethyluronium; FMOC=9-fluorenylmethoxycarbonyl; DIEA=diisopropylethylamine; HOBT=1-hydroxybenzotriazole hydrate; DIC=1,3-diisopropylcarbodiimide.

3CP Inhibition Assays and Antiviral Assays The details of the 3CP enzyme assays used and the antiviral assays used are outlined in Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806, the disclosure of which is incorporated by reference herein.

Protein Crystallography

Serotype 2 human rhinovirus 3C protease was incubated with a 3-fold molar excess of compound 4 in the presence of 2% DMSO for 24 hours at 4 degrees C. The complex was concentrated to 10 mg/mL and then passed through a 0.22 $\mu$m cellulose-acetate filter. Crystals were grown at 13 degrees C. using a hanging drop vapor diffusion method in which equal volumes (3 $\mu$L) of the protein/ligand complex and reservoir solution were mixed on plastic coverslips and sealed over individual wells filled with 1 mL of reservoir solution containing 1.2M ammonium sulfate, 0.325 M sodium phosphate, 0.325 M potassium phosphate, 0.1M ADA pH 6.6, and 2.5% (v/v) 1,4-dioxane. A single crystal measuring 0.6 mm×0.4 mm×0.2 mm (space group $P2_12_12$; a=61.22, b=77.71, c=34.35 Å) was prepared for low-temperature data collection by a two-minute immersion in an artificial mother liquor solution consisting of 400 $\mu$L of the reservoir solution mixed with 125 $\mu$L of glycerol, followed by flash freezing in a stream of $N_2$ gas at −170 degrees C. X-ray diffraction data were collected using an MAR imaging plate and processed with DENZO.

Diffraction data were 74% complete to a resolution of 1.85 Å with R(sym)=1.9%. Protein atomic coordinates from the co-crystal structure determination (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806.), were used to initiate rigid body refinement in X-PLOR followed by simulated annealing and conjugate gradient minimization protocols. Placement of the test compound, addition of ordered solvent, and further refinement proceeded as described in Kean, K. M., Teterina, N. L., Marc, D., Girard, M. *Virology* 1991 181 609–619, which is incorporated by reference herein. The final R factor was 20.8% (10680 reflections with F>2_(F)). The root-mean-square deviations from ideal bond lengths and angles were 0.013 Å and 2.6 degrees, respectively. The final model consisted of all atoms for residues 1–180 (excluding the side chain of residue 21) plus 104 water molecules.

Calculations Used in Virtual Library Analysis We selected 3087 primary amines and mercaptans from the ACD. (Available Chemicals Directory 1997 supplied through ISIS Database 2.0 by MDL Information System, San Leandro, Calif.) The library was built with PEONY (an in-house program which synthesizes the 2D virtual library from its fragments); attaching the compounds at the 5-position of the benzamide core. 3D coordinates of the library were generated with CORINA Ver. 1.7. (CORINA 3D-Structure Generator, version 1.7, April 1996, Jens Sadowski and Johann Gesteiger.) The structures were then energy minimized in the Batchmin module of MacroModel (Mohamadi, F., Richards, N. G. J., Guida, W.C., Liskamp, R., Lipton, M., Caufield, C., Chang, G., Hendrickson, T., Still, W. C., "MacroModel—An Integrated Software System for Modeling Organic and Biooganic Molecules Using Molecular Mechanics", *J. Comput. Chem.* (1990), 11, 440.) Ver. 5.5 using the AMBER* force field (atomic charges were the default from the force field). Compounds with favorable predicted binding modes to either the P2 or P4 pocket were selected by a partially fixed docking routine as implemented in AGDOCK. (Gehlhaar, D. K., Verkhivker, G., Rejto, P. A., Sherman, C. A., Fodel, D. A., Fogel, L. J., Freer, S. T., "Molecular recognition of the inhibitor AG-1343 by HIV-1 protease: conformationally flexible docking by evolutionary programming", *Chemistry and Biology* (1995), 5, 317; D. K. Gehlhaar, D. Bouzida, and P. A. Rejto, "Reduced Dimensionality in Ligand-Protein Structure Prediction: Covalent Inhibitors of Serine Proteases and Design of Site-Directed Combinatorial Libraries," ACS Symposium Series on Rational Drug Design, American Chemical Society (1998), accepted for publication.) Each compound was run through the docking process 8 times against the target protein active site from the cocrystal structure of compound 1, with the benzamide core and protein atoms fixed at the coordinates of the cocrystal structure. (Each docking run is an evolutionary programming algorithm in which many trial protein/ligand configurations are generated and energy evaluated. At the end of each run a single ligand conformation is generated. For more details see Matthews, D. A., Smith, W. A., Ferre, R. A., Condon, B., Budahazi, G., Sisson, W., Villafranca, J. E., Janson, C. A., McElroy, H. E., Gribskov, C. L., Worland, S. Structure of Human Rhinovirus 3C Protease Reveals a Trypsin-like Polypeptide Fold, RNA-Binding Site, and Means for Cleaving Precursor Polyprotein. *Cell* 1994, 77, 761–771. All torsions of the 5 position benzamide substituents were flexible during docking. To remove docked structures with highly unfavorable contacts with the target, the fixed ligand atom constraints were removed, and the ligand structures were energy minimized in the context of the rigid protein. Only those structures which after minimization in the protein maintained the coordinates of the benzamide core close to the cocrystal structure (RMS. deviation<=1.0 for heavy atoms) were kept for further analysis. The docked molecules were then scored and ranked using HTS, (Peter W. Rose, Scoring Methods in Ligand Design, 2 nd UCSF Course in Computer-Aided Molecular Design, San Francisco, Calif., 1997.) a program developed in-house for rapidly estimating the free energy of protein-ligand association. Structures with poor HTS scores were discarded; and among the multiple-docked conformations of the same compound, the one with the best HTS score was retained. Final ranking was made on the basis of which compounds satisfied at least one specific hydrogen bond donor or acceptor interaction with protein atoms which are known to form β-strand type interactions with the native peptide substrate, and which fit well into the P2 or P4 pockets, as judged by ligand-protein atom distance criteria to selected protein atoms in the subsite.

EXAMPLES

Exemplary compounds of the invention and their syntheses are described below.

Example 1

3-Carbamoyl-benzaldehyde (Compound 1a)

Oxalyl chloride (13.3 mL, 152 mmol) and DMF (50 μL) were added to suspension of 3-carboxybenzaldehyde (11.4 g, 76.2 mmol) in 200 mL $CH_2Cl_2$ and stirred at 23° C. for 18 h. The resulting clear solution was concentrated, dissolved in 100 mL $CH_2Cl_2$, and concentrated again. The crude acid chloride was dissolved in 20 mL THF, poured into a mixture of concentrated $NH_4OH$ (26 mL, 381 mmol) with 100 mL crushed ice, and allowed to warm to 23° C. with stirring. The mixture was acidified with conc. HCl to pH ~3, then concentrated to remove THF. The resulting aqueous suspension was filtered and the white solid product dried under vacuum to give 7.4 g (65%) of 3-carbamoyl-benzaldehyde compound 1a: $^1$H NMR (DMSO-$d_6$)δ 10.06 (1 H, s), 8.40 (1 H, s), 8.19 (1 H, s), 8.17 (1 H, d, J=6.6 Hz), 8.04 (1 H, d, J=7.7 Hz), 7.69 (1 H, t, J=7.7 Hz), 7.56 (1 H, s); IR (KBr pellet) 3391, 3205, 1711, 1694, 1664, 1385, 1217. Anal. ($C_8H_7NO_2$·0.1$H_2O$) C, H, N.

3-(3-Carbamoylphenyl)-acrylic acid ethyl ester (Compound 1)

Method A: A solution of 3-carbamoyl-benzaldehyde compound 1a (7.38 g, 49.5 mmol) and (carbethoxymethylene) triphenylphosphorane (17.23 g, 49.5 mmol) in 200 mL toluene was heated to reflux for 24 h. After cooling to room temperature, the reaction mixture was partitioned between 750 mL $CH_2Cl_2$ and a mixture of 200 mL water with 200 mL brine. The organic layer was washed again with a mixture of 100 mL water with 100 mL brine, then dried over $MgSO_4$, filtered and concentrated to a crude yellow oil, which crystallized on standing. The combined aqueous layers were filtered, and the insoluble material was combined with the crude solid obtained from the organic layer. The crude product was purified by recrystallization from methanol. A 5.25 g (48%) yield of compound 1 was isolated in two crops as yellow needles: mp 168–170° C.; $^1$H NMR (CDCl$_3$) δ 7.99(1 H, s), 7.80 (1 H, d, J=7.7 Hz), 7.71 (1 H, d, J=11.8 Hz), 7.68 (1 H, s), 7.49 (1 H, t, J=7.7 Hz), 6.52 (1 H, d, J=16.2 Hz), 6.10 (1 H, br s, NH), 5.75 (1 H, br s, NH), 4.28 (2 H, q, J=7.0 Hz), 1.35 (3 H, t, J=7.0 Hz); IR (neat film) 3414, 3177, 1695, 1682, 1639, 1400, 1313, 1215, 1192. Anal. ($C_{12}H_{13}NO_3$) C, H, N.

Compound 1 was also prepared in 78% yield as a white solid using ethyl acrylate in the same procedure (Method B) for the preparation of compound 2 described below.

Example 2

3-Iodo-benzamide (Compound 32)

3-Iodo-benzamide was prepared using a modification of the procedure by Remsen. (Remsen; Reid *Am. Chem. J.* 1899, 21, 289.) 3-Iodo-benzoic acid (28.68 g, 116 mmol) was stirred in $CH_2Cl_2$ (200 mL) at 23° C. under argon. Oxalyl chloride (30.2 mL, 349 mmol) was added slowly, and slow gas evolution was observed. DMF (0.1 mL) was then added, accelerated gas evolution considerably, and the reaction was stirred for. 2 h. Solvent was removed, and the brown oily residue was dissolved in THF (50 mL) and added to a solution of 18% aqueous $NH_4OH$ (260 mL) at 0° C. After stirring the mixture for 15 min, the liquid was decanted off, and the remaining sludge was acidified with 1 N HCl. The white solid was collected by filtration, washed with water, and dried under vacuum to give 25.68 g (90%) of 3-iodo-benzamide compound 32. $^1$H NMR (DMSO-$d_6$) δ 8.21 (1 H, t, J=1.5 Hz), 8.05 (1 H, s), 7.87 (2 H, dd, J=8.1, 1.5 Hz), 7.47 (1 H, s), 7.25 (1 H, t, J=7.8 Hz); IR (KBr) 3343, 3164, 1661, 1628, 1561, 1424, 1389, 1125. Anal. ($C_7H_6INO$) C, H, N.

Example 3

3-(3-Carbamoyl-phenyl)-acrylic acid methyl ester (Compound 2)

Method B: 3-Iodo-benzamide 32 (1.16 g, 4.7 mmol), methyl acrylate (530 μL, 5.87 mmol), palladium(II) acetate (16 mg, 0.071 mmol), and triethylamine (820 μL, 5.87 mmol) were stirred in 10 mL of acetonitrile under argon in a sealed tube at 100° C. for 5 h. The reaction was cooled to 0° C., and the gray precipitate was collected. Recrystallization from methanol gave 425 mg (44%) compound 2 as a white solid. $^1$H NMR (DMSO-$d_6$) δ 8.20 (1 H, s), 8.04 (1 H, s), 7.87 (2 H, dd, J=7.8, 18 Hz), 7.69 (1 H, d, J=16.2 Hz), 7.50 (1 H, t, J=7.8 Hz), 7.47 (1 H, s), 6.73 (1 H, d, J=15.9 Hz), 3.73 (3 H, s); IR (KBr) 3424, 3366, 3173, 2957, 1728, 1659, 1578, 1431, 1399, 1317. Anal. ($C_{11}H_{11}NO_3$·0.2 $H_2O$) C, H, N.

Example 4
3-(3-Carbamoyl-phenyl)-acrylic acid (Compound 33)

Compound 1 (1.75 g, 7.99 mmol) was hydrolyzed in 2:1 0.8 N aqueous NaOH/methanol (48 mL), stirring at 23° C. for 5 h. The solution was then concentrated to ~20 mL volume, cooled to 0° C., and acidified to pH=4 with 1 N HCl. The resulting crystals were collected, washed with 5 mL of cold $H_2O$, and dried under vacuum to give 1.47 g (96%) of 3-(3-carbamoyl-phenyl)-acrylic acid 33 as a white solid. $^1$H NMR (DMSO-$d_6$) d 12.50 (1 H, br s), 8.17 (1 H, s), 8.05 (1 H, s), 7.85 (2 H, dd, J=23.7, 7.8 Hz), 7.61 (1 H, d, J=16.2 Hz), 7.49 (1 H, t, J=7.5 Hz), 7.47 (1 H, s), 6.62 (1 H, d, J=15.6 Hz); IR (KBr) 3451, 3202, 2924, 1690, 1640, 1443, 1395, 1316, 1219. Anal. ($C_{10}H_9NO_3 \cdot 0.25\ H_2O$) C, H, N.

Example 5
3-(3-Carbamoyl-phenyl)-adrylic acid benzyl ester (Compound 3)

3-(3-Carbamoyl-phenyl)-acrylic acid (212 mg, 1.11 mmol) and benzyl alcohol (172 mL, 1.66 mmol) were stirred in DMF (3 mL) at 0° C. EDC (318 mg, 1.66 mmol), triethylamine (170 μL, 1.22 mmol), and DMAP (14 mg, 0.11 mmol) were added, and the reaction was allowed to stir for 3 h while warming to 23° C. The solution was concentrated, and the residue was purified by flash chromatography (3% EtOH/CHCl$_3$) to give 90 mg (29%) of compound 3 as a white solid. $^1$H NMR (DMSO-$d_6$) δ 8.22 (1 H, s), 8.04 (1 H, s), 7.94 (2 H, dd, J=12.0, 7.8 Hz), 7.61 (1 H, d, J=16.2 Hz), 7.34–7.50 (7 H, m), 6.79 (1 H, d, J=16.2 Hz), 5.23 (2 H, s); IR (KBr) 3420, 3316, 3150, 1711, 1665, 1630, 1402, 1308, 1167. Anal. ($C_{17}H_{15}NO_3$) C, H, N.

Example 6
3-(3-Carbamoyl-phenyl)-acrylic acid 2-hydroxyethyl ester (Compound 4)

This compound was prepared in 33% yield as a white solid using ethylene glycol in a procedure analogous to that for preparing compound 3 as described above. $^1$H NMR (DMSO-$d_6$) δ 8.21 (1 H, s), 8.06 (1 H, s), 7.88 (2 H, dd, J=16.2, 7.5 Hz), 7.70 (1 H, d, J=16.2 Hz), 7.46–7.53 (7 H, m), 6.74 (1 H, d, J=16.2 Hz), 4.87 (1 H, br s), 4.16 (2 H, t, J=4.9 Hz), 3.63 (2 H, t, J=5.1 Hz); IR (KBr) 3418, 3212, 1705, 1676, 1626, 1574, 1399, 1280. Anal. ($C_{12}H_{13}NO_4$) C, H, N.

Example 7
3-(3-Carbamoyl-phenyl)-acrylic acid phenethyl ester (Compound 5)

This compound was prepared in 49% yield as a white solid using phenethyl alcohol in the same procedure for the preparation of compound 3 described above. $^1$H NMR (CDCl$_3$) δ 7.98 (1 H, s), 7.79 (1 H, d, J=7.8 Hz), 7.68 (1 H, d, J=16.2 Hz), 7.66 (1 H, d, J=7.8 Hz), 7.48 (1 H, t, J=7.5 Hz), 7.23–7.36 (5 H, m), 6.50 (1 H, d, J=16.2 Hz), 6.14 (1 H, br s), 5.83 (1 H, br s), 4.44 (2 H, t, J=6.9 Hz), 3.02 (2 H, t, J=6.9 Hz); IR (KBr) 3410, 3165, 1705, 1678, 1630, 1576, 1393, 1373, 1283, 1261. Anal. ($C_{18}H_{17}NO_3$) C, H, N.

Example 8
3-(3-Carbamoyl-phenyl)-acrylic acid pyridin-3-yl methyl ester (Compound 6)

This compound was prepared in 68% yield as a white solid using 3-pyridyl carbinol in the same procedure for the preparation of compound 3 described above. $^1$H NMR (CDCl$_3$) δ 8.68 (1 H, s), 8.60 (1 H, d, J=4.8 Hz), 7.99 (1 H, s), 7.66–7.81 (4 H, m), 7.48 (1 H, t, J=7.5 Hz), 7.26–7.35 (1 H, m), 6.55 (1 H, d, J=16.2 Hz), 6.16 (1 H, br s), 5.79 (1 H, br s), 5.28 (2 H, s); IR (KBr) 3418, 3160, 1700, 1676, 1630, 1576, 1397, 1285, 1259. Anal. ($C_{16}H_{14}N_2O_3$) C, H, N.

Example 9
3-(2-Ethoxycarbonyl-vinyl)-benzoic acid (Compound 7)

Using Method B described above, compound 7 was prepared in 72% yield as a white solid. $^1$H NMR (CDCl$_3$) δ 11.22 (1 H, s), 8.29 (1 H, s), 8.13 (1 H, d, J=7.8 Hz), 7.71–7.78 (2 H, m), 7.52 (1 H, t, J=7.5 Hz), 6.54 (1 H, d, J=16.2 Hz), 4.29 (2 H, q, J=7.2 Hz ), 1.36 (3 H, t, J=7.2 Hz); IR (KBr) 2984, 2672, 2564, 1725, 1642, 1445, 1302, 1209, 1177 cm$^{-1}$. Anal. ($C_{12}H_{12}O_4 \cdot 0.2\ H_2O$) C, H.

Example 10
3-(2-Ethoxycarbonyl-vinyl)-benzoic acid methyl ester (Compound 8)

Compound 7 (225 mg, 1.02 mmol) was dissolved in a mixture of dichloromethane (2 mL) and methanol (2 mL). (Trimethylsilyl)diazomethane (2 M solution in hexanes, ~0.8 mL, ~1.6 mmol) was added dropwise until gas evolution ceased and a faint yellow color remained for 10 min. The reaction was concentrated and purified by flash chromatography (1% MeOH/CHCl$_3$) to give 196 mg (82%) of 8 as a white solid. $^1$H NMR (CDCl$_3$) δ 8.21 (1 H, s), 8.05 (1 H, d, J=7.8 Hz), 7.71 (1 H, d, J=16.2 Hz), 7.70 (1 H, d, J=7.8 Hz), 7.47 (1 H, t, J=7.8 Hz), 6.50 (1 H, d, J=16.3), 4.28 (2 H, q, J=7.2 Hz), 1.35 (3 H, t, J=7.2 Hz); IR (KBr) 3399, 3094, 3065, 3034, 2980, 2907, 1717, 1638, 1447 cm$^{-1}$. Anal. ($C_{13}H_{14}O_4$) C, H.

Example 11
(E)-3-(3-Carbamoyl-phenyl)-2-cyano-acrylic acid ethyl ester (Compound 9)

Piperidine (150 μL, 1.52 mmol) was added to a solution of 3-formyl benzamide compound 30 (111 mg, 0.74 mmol) and ethyl cyanoacetate (79 μL, 0.74 mmol) in ethanol (2 mL) at 0° C. After stirring for 5 h at 23° C., solvent was removed. The residue was dissolved in CH$_2$Cl$_2$ and washed with 0.1 N HCl, H$_2$O, and then brine. Organics were dried (Na$_2$SO$_4$) and concentrated. Purification by flash chromatography (3% MeOH/CHCl$_3$) gave 86 mg (47%) of 9 as a white solid. $^1$H NMR (CDCl$_3$) δ 8.37 (1 H, s), 8.31 (1 H, s), 8.18 (1 H, d, J=7.8 Hz), 8.04 (1 H, d, J=7.8 Hz), 7.63 (1 H, t, J=7.8 Hz), 6.09 (1 H, br s), 5.71 (1 H, br s), 4.41 (2 H, q, J=7.2 Hz), 1.42 (3 H, t, J=7.2 Hz). IR (KBr) 3435, 3351, 3306, 3167, 2224, 1724, 1701, 1626, 1601, 1578, 1433, 1383, 1275, 1211 cm$^{-1}$. Anal. ($C_{13}H_{12}N_2O_3 \cdot 0.5\ H_2O$) C, H, N.

Example 12
6-Methyl-3-(3-carbamoylphenyl)-acrylic acid ethyl ester (Compound 10)

3-Iodo-4-methyl benzoic acid was converted to the corresponding benzamide according to the procedure described for compound 1a above ((COCl)$_2$, NH$_4$OH), to provide 3-iodo-4-methyl benzamide in 93% yield. Further conversion according to Method B described above provided compound 10 in 48% yield. $^1$H NMR (CDCl$_3$) δ 8.02 (1 H, d, J=1.6 Hz), 7.95 (1 H, d, J=7.9 Hz), 7.29 (1 H, d, J=7.9 Hz), 6.46 (1 H, d, J=15.9 Hz), 6.10 (1 H, br s), 5.75 (1 H, br s), 4.08 (2 H, q, J=7.1 Hz), 2.48 (3 H, s), 1.42 (3 H, t, J=7.1 Hz) Anal. ($C_{13}H_{12}N_2O_3 \cdot 0.2\ H_2O$) C, H, N.

Example 13
3-Methoxy-5-nitro-phenylamine (Compound 34)

Sodium bicarbonate (6.07 g, 72.3 mmol) was added to sodium sulfide nonahydrate (18.2 g, 75.9 mmol) in deionized water (50 mL). When the sodium bicarbonate was completely dissolved, methanol (50 mL) was added, and the solution cooled to 0° C. A precipitate formed, which was removed by filtration through a Celite pad; the filtered solution was added to 3,5-dinitroanisole (8.02 g, 40.5 mmol) in methanol (50 ML). After heating at reflux for 30 min, the solution was concentrated in vacuo to remove methanol. The aqueous residue was poured into 200 mL ice-water, and the resulting orange precipitate was collected by suction filtration. Chromatography (1:2 EtOAc/hexanes) of the crude solid yielded unreacted 3,5-dinitroanisole (0.98 g, 12%) and aniline product compound 34 (4.96 g, 73%; 83% based on recovered 3,5-dinitroanisole) as an orange solid. mp 117–119° C.; $^1$H NMR (CDCl$_3$) δ 7.12 (s, 2 H), 6.48 (s, 1 H), 3.98 (br s, 2 H), 3.83 (s, 3 H); IR (KBr pellet) 3447, 3364, 1637, 1523, 1344 cm$^{-1}$; Anal. (C$_7$H$_8$N$_2$O$_3$) C, H, N.

Example 14
1-Iodo-3-methoxy-5-nitro-benzene (Compound 35)

Concentrated HCl (15 mL) was added to a solution of aniline compound 34 (5.25 g, 31.2 mmol) in water (15 mL) at 0° C. To this was added a chilled solution of sodium nitrite (3.88 g, 56.2 mmol) in water (20 mL), dropwise, with vigorous mechanical stirring. Stirring was continued at 0° C. for 15 min. after the addition was complete, and then a solution of potassium iodide (10.37 g, 62.4 mmol) in water (20 mL) was added carefully. The cooling bath was removed, and the reaction heated to boiling. When the production of purple vapor ceased, the mixture was cooled to 23° C. and extracted with CH$_2$Cl$_2$ (3×200 mL). The combined organic extracts were dried (MgSO$_4$), filtered, and concentrated in vacuo. Purification by silica gel chromatography (1:9 EtOAc/hexanes) gave pure iodide compound 35 (7.35 g, 84%) as a colorless solid. mp=81–82° C.; $^1$H NMR (CDCl$_3$) δ 8.15 (s, 1 H), 7.70 (s, 1 H), 7.56 (s, 1 H), 3.88 (s, 3 H); IR (KBr pellet) 1527, 1342 cm$^{-1}$; Anal. (C$_7$H$_6$INO$_3$) C, H, N.

Example 15
3-Iodo-5-methoxy-phenylamine (Compound 36)

A mixture of triirondodecacarbonyl (16.24 g, 32.2 mmol), compound 35 (7.50 g, 26.9 mmol), methanol (15 mL), and toluene (200 mL) was heated at reflux for 3.5 h. After cooling, filtration, concentration in vacuo, and silica gel chromatography (1:4 EtOAc/hexanes), aniline compound 36 (6.11 g, 91%) was obtained as a yellow oil, which crystallized on standing. mp=84–86° C.; $^1$H NMR (CDCl$_3$) δ 6.64 (s, 2), 6.15 (s, 1 H), 3.71 (s, 3H), 3.66 (br s, 2H);); IR (KBr pellet) 3414, 3308, 3208, 1572 cm$^{-1}$; Anal. (C$_7$H$_8$INO) C, H, N.

Example 16
3-Amino-5-methoxy-benzonitrile (Compound 37)

By the same method used to make compound 44, iodide compound 36 (2.51 g, 10.1 mmol) was converted to nitrile compound 37 (1.24 g, 83%), a yellow solid. mp=81–85° C.; $^1$H NMR (CDCl$_3$) δ 6.53 (m, 2H), 6.39 (t, , J=2.0 Hz, 1H), 3.87 (br s, 2H), 3.77 (s, 3H); IR (neat film) 3408, 3333, 3221, 2228, 1597 cm$^{-1}$; Anal. (C$_8$H$_8$N$_2$O) C, H, N.

Example 17
3-Iodo-5-methoxy-benzonitrile (Compound 38)

By the same method used to prepare compound 35, nitrile compound 37 (1.12 g, 7.6 mmol) was converted to iodide compound 38 (1.25 g, 64%). $^1$H NMR (CDCl$_3$) d 7.55 (s, 1H), 7.47 (s, 1H), 7.12 (s, 1H), 3.82 (s. 3H); IR (neat film) 2231, 1587, 1284 cm$^{-1}$; Anal. (C$_8$H$_6$INO) C, H, N.

Example 18
3-Iodo-5-methoxy-benzamide (Compound 39)

By the same method used to prepare amide compound 45, nitrile compound 38 (1.245 g, 4.81 mmol) was converted to amide compound 39 (1.039 g, 78%), a white solid. mp=175–176° C.; $^1$H NMR (CDCl$_3$) δ 7.65 (s, 1 H), 7.40 (s, 1 H), 7.34 (s, 1 H), 6.0–5.8 (2 br S, 2 H), 3.83 (s, 3 H); IR (KBr pellet) 3389, 3194, 1658, 1568, 1390 cm$^{-1}$; Anal. (C$_8$H$_8$INO$_2$) C, H, N.

Example 19
3-Hydroxy-5-iodo-benzamide (Compound 40)

Amide compound 39 (1.032 g, 3.72 mmol) suspended in CH$_2$Cl$_2$ (100 mL) was cooled to −78° C. Boron tribromide solution (1.0 M in CH$_2$Cl$_2$, 7.45 mL, 7.45 mmol) was added. After stirring at −78° C. for 30 min, the solution was heated to reflux for 4 h. Another equivalent of boron tribromide (3.7 mL) was added, and the solution stirred at 23° C. for 16 h. The reaction mixture was quenched with water (50 mL), causing a white precipitate to form. Ether (50 mL) was added to dissolve the precipitate, and the layers separated. The aqueous layer was discarded, and the ether layer washed with 2N NaOH (2×100 ml). The combined basic washes were treated with 6 N HCl until pH ~4, then extracted with ether (2×150 ml). These ether extracts were dried (MgSO$_4$), filtered and concentrated in vacuo to give phenol compound 40 (803.3 mg, 82%) as a white solid. mp=192–195° C.; $^1$H NMR (DMSO-d$_6$) δ 9.99 (s, 1H), 7.93 (s, 1H), 7.61 (s, 1H), 7.37 (s, 1H), 7.24 (s, 2H) ); IR (KBr pellet) 3483, 3396, 3232, 1680, 1649, 1433 cm$^{-1}$; Anal. (C$_7$H$_6$INO$_2$) C, H, N.

Example 20
3-(3-Carbamoyl-5-hydroxy-phenyl)-acrylic acid ethyl ester (Compound 11)

Iodide compound 40 (24.6 mg, 0.093 mmol) was coupled 10 with ethyl acrylate (23.4 mg, 0.234 mmol) under the standard conditions described above to give compound 11 (17.3 mg, 79%) as a white solid. mp=200–202° C.; $^1$H NMR (DMSO-d$_6$) δ 9.86 (s, 1 H), 7.92 (s, 1H), 7.67 (s, 1H), 7.57 (d, J=16.8 Hz, 1H), 7.36 (s, 1H), 7.31 (s, 1H), 7.15 (s, 1H), 6.61 (d, J=16.2 Hz, 1H), 4.18 (q, J=7.0 Hz, 2H), 1.25 (t, J=7.0 Hz, 3H) ); IR (KBr pellet) 3402, 3209, 1680, 1593, 1296 cm$^{-1}$; Anal. (C$_{12}$H$_{13}$NO$_4$•0.4H$_2$O) C, H, N.

Example 21
3-Benzyloxy-5-iodo-benzamide (Compound 49)

A solution of benzyl bromide (128 mg, 0.75 mmol), phenol compound 40 (131.5 mg, 0.50 mmol), and potassium carbonate (138 mg, 1.00 mmol) in DMF (3.0 mL) was heated to 60° C. for 1.5 h. After cooling to 23° C., the solution was filtered, concentrated in vacuo, and purified by silica gel chromatography (1:1 EtOAc/hexanes) to give benzyl ether compound 49 (132.5 mg, 75%) as a white solid. mp=124–125° C.; $^1$H NMR (CDCl$_3$) δ 7.67 (s, 1H), 7.49 (s, 1H), 7.40 (m, 6H), 6.0–5.8 (2 br s, 2H), 5.08 (s, 2H); IR (KBr pellet) 3369, 3192, 1660, 1564 cm$^{-1}$; Anal. (C$_{14}$H$_{12}$INO$_2$) C, H, N.

Example 22
3-(3-Benzyloxy-5-carbamoyl-phenyl)-acrylic acid ethyl ester (Compound 12)

Iodide compound 49 (51.6 mg, 0.146 mmol) was coupled with ethyl acrylate (36.6 mg, 0.365 mmol) under the standard conditions to give compound 12 (18.5 mg, 39%) as an off-white solid. mp=193–194° C.; $^1$H NMR (DMSO-d$_6$) δ 8.01 (s, 1H), 7.81 (s, 1H), 7.63 (d, J=15.8 Hz, 1H), 7.54 (d, J=4.8 Hz, 2H), 7.45 (m, 6H), 6.75 (d, J=15.8 Hz, 1H), 5.18 (s, 2H), 4.19 (q, J=7.0 Hz, 2H), 1.26 (t, J=7.0 Hz, 3H) ); IR (KBr pellet) 3418, 3173, 1705, 1670, 1589, 1288 cm$^{-1}$; Anal. ($C_{19}H_{19}NO_4 \cdot 0.2H_2O$) C, H, N.

Example 23
3-Carbamoyl-4-methoxy-benzaldehyde (Compound 41)

3-Bromo-anisaldehyde (8.0 g, 37.2 mmol) and copper cyanide (4.0 g, 44.67 mmol) were stirred in DMF (100 mL) at 150° C. for 16 h. To this was added an iron nitrate solution (20 g iron(III) nitrate, 6 mL concentrated HCl, 40 mL $H_2O$), and the mixture stirred 10 min before it was allowed to cool to 23° C. The reaction was then diluted with $H_2O$ (200 mL) and extracted with $CHCl_3$ (3×80 mL). organic layers were combined and solvents were removed, taking care to pump off the residual DMF. The brown-green residue was once again dissolved in $CHCl_3$ (100 mL) and washed with 1 N HCl (50 mL) and brine (50 mL). The material was dried ($Na_2SO_4$), and solvent was removed to give the crude nitrile as a tan solid. The nitrile was stirred in concentrated $H_2SO_4$ (60 mL) at 100° C. for 1 h. The solution was cooled, poured into $H_2O$ (250 mL), and extracted with $CHCl_3$ (8×50 mL). Organics were dried ($Na_2SO_4$) and concentrated. The resulting solid was recrystallized from methanol to give 2.98 g (45%) of 3-carbamoyl-4-methoxy-benzaldehyde 41 as a white solid. $^1H$ NMR ($CDCl_3$) δ 9.92 (1 H, s), 8.28 (1 , s), 8.00 (1 H, d, J=9.0 Hz), 7.74 (1 H, br s), 7.69 (1 H, br s), 7.33 (1 H, d, J=9.0 Hz), 3.98 (3 H, s); IR (KBr) 3399, 3183, 1676, 1589, 1433, 1262, 1204 cm$^{-1}$. Anal. ($C_9H_9NO_3$) C, H, N.

Example 24
5-Formyl-2-hydroxy-benzamide (Compound 42)

3-Carbamoyl-4-methoxy-benzaldehyde compound 41 (1.065 g, 5.95 mmol) was stirred in dry $CH_2Cl_2$ (120 mL) at −78° C. under argon. Boron tribromide (10.71 mL, 1.0 M, 10.71 mmol) was added, and the reaction stirred 18 h while warming to 23° C. The reaction was quenched with 0.05 N HCl (80 mL), and was allowed to stir for 15 min. The organic layer was collected, and the aqueous layer was further extracted with EtOAc (2×50 mL). Organics were combined, dried ($Na_2SO_4$), and concentrated. Purification by flash chromatography (60% EtOAc/$CHCl_3$) gave 540 mg (55%) of 5-formyl-2-hydroxy-benzamide 42 as a white solid. $^1H$ NMR (DMSO-$d_6$) δ 14.00 (1 H, s), 9.88 (1 H, s), 8.73 (1 H, br s), 8.55 (1 H, d, J=1.5 Hz), 8.21 (1 H, br s), 8.00 (1 H, dd, J=8.7, 1.5 Hz), 7.13 (1 H, d, J=8.7 Hz); IR (KBr) 3420, 3237, 1686, 1618, 1493, 1375, 1279, 1196 cm$^{-1}$. Anal. ($C_8H_7NO_3$) C, H, N.

Example 25
3-(3-Carbamoyl-4-hydroxy-phenyl)-acrylic acid ethyl ester (Compound 14)

5-Formyl-2-hydroxy-benzamide compound 42 (65 mg, 0.40 mmol) and (carbethoxy-methylene) triphenylphosphorane (281 mg, 0.81 mmol) were stirred in DMF (3 mL) at 23° C. for 2 h. Solvent was removed, and the residue was purified by flash chromatography (2% MeOH/$CHCl_3$) to give 44 mg (48%) of compound 14 as a white solid. $^1H$ NMR (DMSO-$d_6$) δ 13.50 (1 H, s), 8.52 (1 H, br s), 8.29 (1 H, s), 8.07 (1 H, br s), 7.77 (1 H, d, J=8.7 Hz), 7.56 (1 H, d, J=15.6 Hz), 6.92 (1 H, d, J=8.7 Hz), 6.57 (1 H, d, J=15.6 Hz), 4.18 (2 H, q, J=7.2 Hz), 1.26 (3 H, t, J=7.2); IR (KBr) 3387, 3198, 2988, 2359, 1688, 1620, 1491, 1441, 1372, 1279 cm$^{-1}$. Anal. ($C_{12}H_{13}NO_4$) C, H, N.

Example 26
2-Benzyloxy-5-formyl-benzamide (Compound 42a)

Compound 42 (105 mg, 0.64 mmol) and benzyl bromide (114 μL, 0.95 mmol) were stirred in DMF (3 mL) with $K_2CO_3$ (176 mg, 1.27 mmol) at 60° C. for 1 h. Solvent was removed, and the residue was purified by flash chromatography (2% MeOH/$CHCl_3$) to give 135 mg (83%) of 42a as a white solid. $^1H$ NMR (DMSO-$d_6$) δ 9.91 (1 H, s), 8.24 (1 H, s), 7.98 (1 H, d, J=8.7 Hz), 7.67 (2 H, br s), 7.51 (2 H, d, J=7.2 Hz), 7.41–7.34 (4 H, m), 5.36 (2 H, s); IR (KBr) 3387, 3192, 2849, 1690, 1649, 1599, 1437, 1389, 1265, 1206 cm$^{-1}$. Anal. ($C_{15}H_{13}NO_3 \cdot 0.2 H_2O$) C, H, N. Calculated C=69.59, H=5.22, N=5.41; found C=69.60, H=5.21, N=5.42.

Example 27
3-(4-Benzyloxy-3-carbamoyl-phenyl)-acrylic acid ethyl ester (Compound 15)

2-benzyloxy-5-formyl-benzamide compound 42a (105 mg, 0.412 mmol) and (carbethoxy-methylene) triphenylphosphorane (287 mg, 0.824 mmol) were stirred in DMF (3 mL) at 40° C. for two hours. Solvent was removed, and the residue was purified by flash chromatography (1% MeOH/$CHCl_3$) to give 95.8 mg (72%) of compound 15 as a white solid. $^1H$ NMR ($CDCl_3$) δ 8.45 (1 H, d, J=1.8 Hz), 7.70–7.60 (3 H, m), 7.43 (5 H, br s), 7.08 (1 H, d, J=8.7 Hz), 6.43 (1 H, d, J=15.6 Hz), 5.75 (1 H, br s), 5.23 (2 H, s), 4.25 (2 H, q, J=7.2 Hz), 1.33 (3 H, t, J=7.2 Hz); IR (KBr) 3441,3154, 1689, 1676, 1593, 1500, 1431, 1371 cm$^{-1}$. Anal. ($C_{19}H_{19}NO_4$) C, H, N.

Example 28
3-[2-(Methoxy-methyl-carbamoyl)-vinyl] benzamide (Compound 43)

3-Iodo-benzamide compound 32 (3.0 g, 12.1 mmol), N-methoxy-N-methylacrylamide (Molander, G. G.; Stengel, P. J. Tetrahedron 1997, 53, 26, 8887–8912.) (1.8 g, 15 mmol), palladium (II) acetate (40 mg, 0.18 mmol), and triethylamine (2.1 mL, 15 mmol) were stirred in acetonitrile (12 mL) under argon in a sealed tube at 100° C. for 2.5 h. The reaction was allowed to cool, and solvent was removed. The residue was dissolved in $CH_2Cl_2$, washed with 0.1 N HCl and then with brine, dried ($MgSO_4$), and concentrated. Recrystallization twice from methanol gave 1.64 g (58%) of 3-[2-(methoxy-methylcarbamoyl)-vinyl]benzamide 43 as a white solid. $^1H$ NMR ($CDCl_3$) δ 8.06 (1 H, s), 7.78 (1 H, d, J=7.8 Hz), 7.73 (1 H, d, J=16.2 Hz), 7.69 (1 H, d, J=7.8 Hz), 7.46 (1 H, t, J 7.8 Hz), 7.10 (1 H, d, J=16.2 Hz), 6.33 (1 H, br s), 5.97 (1 H, br s), 3.77 (3 H, s), 3.31 (3 H, s); IR (KBr) 3385, 3173, 1680, 1649, 1613, 1582, 1476, 1433, 1397, 1182, 1105 cm$^{-1}$. Anal. ($C_{12}H_{14}N_2O_3 \cdot 0.33 H_2O$) C, H, N.

Example 29
3-(3-Oxo-but-1-enyl)-benzamide (Compound 16)

Method C: 3-[2-(Methoxy-methyl-carbamoyl)-vinyl] benzamide compound 43 (100 mg, 0.427 mmol) was stirred in dry THF (4 mL) at 0° C. under argon. Methyllithium (1.6 mL, 1.5 M in ether, 2.4 mmol) was added, and the reaction stirred for 1.5 h. The reaction was poured over 0.1N HCl and extracted with $CH_2Cl_2$. Organics were dried ($MgSO_4$) and concentrated. Purification by flash chromatography (2 to 5% EtOH/$CH_2Cl_2$) gave 54 mg (67%) of 16 as a white solid. $^1H$ NMR ($CDCl_3$) δ 8.03 (1 H, s), 7.80 (1 H, d, J=7.8 Hz), 7.70 (1 H, d, J=7.8 Hz), 7.54 (1 H, d, J=16.2 Hz), 7.50 (1 H, t, J=7.8 Hz), 6.80 (1 H, d, J=16.2 Hz), 6.14 (1 H, br s), 5.82 (1 H, br s), 2.39 (3 H, s); IR (KBr) 3345, 3160, 2363, 1667, 1400, 1264 cm$^{-1}$. Anal. ($C_{11}H_{11}NO_2$) C, H, N.

Example 30
3-(3-Oxo-3-phenyl-prop-1-enyl)-benzamide (Compound 17)

Compound 17 was prepared in 20% yield as a white solid using phenyllithium according to Method C described above. $^1$H NMR (CDCl$_3$) δ 8.15 (1 H, s), 8.03 (2 H, d, J=7.2 Hz), 7.76–7.84 (3 H, m), 7.48–7.64 (5 H, m), 6.26 (1 H, br s), 5.85 (1 H, br s). IR (KBr) 3383, 3192, 3057, 2361, 1653, 1609, 1580, 1447 cm$^{-1}$. Anal. (C$_{16}$H$_{13}$NO$_2$) C, H, N.

Example 31
3-[3-(4-Dimethylamino-phenyl)-oxo-propenyl] benzamide (Compound 18)

4-Bromo-N,N-dimethylaniline (770 mg, 3.85 mmol) was stirred in dry THF (6 mL) at −40° C. under argon. n-Butyllithium (1.5 mL, 2.5 M in hexanes, 3.75 mmol) was added dropwise, and the solution stirred for 15 min. A solution of 3-[2-(methoxy-methyl-carbamoyl)vinyl] benzamide compound 43 (150 mg, 0.64 mmol) in THF (3 mL) was added slowly, and the reaction stirred for 1 h while warming to 23° C. The reaction was poured over saturated NH$_4$Cl, and was then extracted with CHCl$_3$. Organics were washed with brine, dried (Na$_2$SO$_4$), and concentrated. Purification by flash chromatography (1 to 4% MeOH/CHCl$_3$) gave 140 mg of 18 (74%) as a bright orange solid. $^1$H NMR (CDCl$_3$) δ 8.14 (1 H, s), 8.02 (2 H, d, J=9.0 Hz), 7.83–7.75 (3 H, m), 7.67 (1 H, d, J=15.6 Hz), 7.50 (1 H, t, J=7.8 Hz), 6.71 (2 H, d, J=9.0 Hz), 6.13 (1 H, br s), 5.66 (1 H, br s), 3.10 (6 H, s); IR (KBr) 3372, 3192, 1671, 1609, 1578, 1377, 1188 cm$^{-1}$. Anal. (C$_{18}$H$_{18}$N$_2$O$_2$.0.1 H$_2$O) C, H, N.

Example 33
3-[3-(4-Methoxy-phenyl)-oxo-propenyl] benzamide (Compound 19)

Compound 19 was prepared in 47% yield as a white solid using 4-bromoanisole in the same procedure for the preparation of 18 described above. $^1$H NMR (CDCl$_3$) δ 8.15 (1 H, s), 8.06 (2 H, d, J=8.7 Hz), 7.84–7.75 (3 H, m), 7.63 (1 H, d, J=16.2 Hz), 7.51 (1 H, t, J=7.8 Hz), 6.99 (2 H, d, J=9.0 Hz), 6.18 (1 H, br s), 5.73 (1 H, br s), 3.90 (3 H, s); IR (KBr) 3376, 3192, 1659, 1607, 1439, 1227 cm$^{-1}$. Anal. (C$_{17}$H$_{15}$NO$_3$.0.2 H$_2$O) C, H, N.

Example 34
3-(3-Oxo-3-pyridin-2-yl-propenyl)-benzamide (Compound 20)

This compound was prepared in 17% yield as a white solid using 2-bromopyridine in the same procedure for the preparation of compound 18 described above. $^1$H NMR (CDCl$_3$) δ 8.76 (1 H, d, J=4.8 Hz), 8.39 (1 H, d, J=16.2 Hz), 8.19 (2 H, t, J=1.5 Hz), 7.95 (1 H, d, J=16.2 Hz), 7.91–7.82 (3 H, m), 7.52 (2 H, t, J=7.8 Hz), 6.26 (1 H, br s), 5.91 (1 H, br s); IR (KBr) 3416, 3207, 3055, 1672, 1607, 1580, 1391, 1332, 1221 cm$^{-1}$. Anal. (C$_{15}$H$_{12}$N$_2$O$_2$. 0.2 H$_2$O) C, H, N.

Example 35
3-(3-Furan-2-yl-3-oxo-propenyl)-benzamide (Compound 21)

To a solution of freshly distilled furan (425 µL, 5.85 mmol) in dry THF (8 mL) at −10° C. under argon, was added n-butyllithium (1.56 mL, 2.5 M in hexanes, 3.9 mmol).[13] After stirring for 2 h at 0° C., the solution was cooled to −50° C., and a solution of 3-[2-(methoxy-methylcarbamoyl)-vinyl]benzamide (114 mg, 0.487 mmol) in THF(1 mL) was added slowly. The reaction stirred 1 h while warming to 0° C., and was then poured over saturated NH$_4$Cl and extracted with CHCl$_3$. Organics were washed with brine, dried (Na$_2$SO$_4$) and concentrated. Purification by flash chromatography (2 to 6% MeOH/CHCl$_3$) gave 49 mg (42%) of compound 21 as a white solid. $^1$H NMR (CDCl$_3$) δ 8.16 (1 H, s), 7.89 (1 H, d, J=15.6 Hz), 7.83–7.76 (2 H, m), 7.68 (1 H, t, J=0.9 Hz), 7.57–7.48 (2 H, m), 7.37 (1 H, d, J=3.6 Hz), 6.62 (1 H, dd, J=2.1, 0.9 Hz), 6.15 (1 H, br s), 5.69 (1 H, br s); IR (KBr) 3474, 3354, 3191, 1668, 1605, 1466, 1393, 1325 cm$^{-1}$. Anal. (C$_{14}$H$_{11}$NO$_3$.0.2 H$_2$O) C, H, N.

Example 36
1-Oxo-indan-5-carbonitrile (Compound 44)

A solution of 5-bromo-1-indanone (5.28 g, 25 mmol, zinc cyanide (1.76 g, 15 mmol), and tetrakis (triphenylphosphine) palladium (0) (1.15 g, 1.0 mmol) in DMF (25 mL) was heated to 80° C. for 2 h. After cooling to 23° C., the solution was diluted with toluene (50 mL), washed with 2N NH$_4$OH (2×50 mL) and brine (50 mL), dried over MgSO$_4$, filtered and concentrated in vacuo. Chromatography of the residue (1:1 EtOAc/hexanes) yielded 3.33 g (85%) of compound 44 as a yellow solid. $^1$H NMR (CDCl$_3$) δ 7.85 (d, J=7.7 Hz, 1H), 7.82 (s, 1H), 7.67 (d, J=7.7 Hz, 1H), 3.21 (t, J=5.9 Hz, 2H), 2.77 (dd, J=6.3, 5.9 Hz, 2H); IR (KBrpellet) 2226, 1715 cm$^{-1}$; Anal. (C$_{10}$H$_7$NO•0.1H$_2$O) C, H, N.

Example 37
1-Oxo-indan-5-carboxylic acid amide (Compound 45)

A solution of nitrile, compound 44, (3.02 g, 20.4 mmol) in 3% aqueous H$_2$O$_2$ (110 mL) was heated at 50° C. for 4 h. The mixture was then cooled to 0° C. for 1 h, and the resulting precipitate collected by suction filtration, and dried under vacuum to give 2.40 g (67%) of compound 45 as a yellow solid. The aqueous mother liquor was concentrated to dryness and triturated with hot methanol. The methanol solubles were concentrated and purified by silica gel chromatography (5% MeOH in CH$_2$Cl$_2$) to give 184.5 mg (5%) more compound 45 as a white solid. mp=207° C.; $^1$H NMR (DMSO-d$_6$) δ 8.14 (s,1H), 8.02 (s, 1H), 7.85 (d, J=7.7 Hz, 1H), 7.67 (d, J=7.7 Hz, 1 H), 7.57 (s, 1H), 3.13 (t, J=5.7 Hz, 2 H), 2.68 (m, 2 H); IR (KBr pellet) 1697, 1660, 1622 cm$^{-1}$; Anal. (C$_{10}$H$_9$NO$_2$) C, H, N.

Example 38
1-Oxo-indan-5-carboxylic acid trityl-amide (Compound 46)

Acetic anhydride (1.05 mL, 11.1 mmol) and concentrated H$_2$SO$_4$ (0.01 mL) were added to a solution of amide compound 45 (620.5 mg, 3.54 mmol) and triphenylmethyl alcohol (615 mg, 2.36 mmol) in glacial acetic acid (12 mL).[12] The solution was heated at 40° C. for 3.5 h, cooled to 23° C., and concentrated in vacuo. The residue was purified by silica gel chromatography (1:1 EtOAc/hexanes to 10:1 EtOAc/hexanes) to give 432 mg (44% based on trityl alcohol) compound 46 as a yellow solid. $^1$H NMR (CDCl$_3$) δ 7.92 (s, 1H), 7.78 (q, J=8.5 Hz, 2H), 7.30 (m, 15H), 3.18 (t, J=5.9 Hz, 2H), 2.74 (m, 2H); Anal. (C$_{29}$H$_{23}$NO$_2$•0.25H$_2$O) C, H, N.

Example 39
1-Oxo-1H-indene-5-carboxylic acid trityl-amide (Compound 47)

A solution of N-bromosuccinimide (67.3 mg, 0.38 mmol) and amide compound 46 (157.8 mg, 0.38 mmol) in CCl$_4$ (10 mL) was heated to reflux for 2 h while irradiated with a 200 w lamp. After cooling to 23° C., the succinimide precipitate was filtered off. The clear solution was cooled to 0° C. and treated with triethylamine (0.055 mL, 0.40 mmol) for 2 h, then concentrated in vacuo. Chromatography of the residue (1:1 EtOAc/hexanes) afforded 73.6 mg (47%) enone compound 47 as a yellow solid. $^1$H NMR (CDCl$_3$) d 7.66 (d, J=7.3 Hz, 1H), 7.61 (d, J=5.9 Hz, 1H), 7.51 (s, 1 H), 7.47 (d, J=7.3 Hz, 1H), 7.28 (m, 16H), 5.98 (d, J=5.9 Hz, 1H); IR (neat film) 1711, 1670, 1493 cm$^{-1}$.

Example 40
1-Oxo-1H-indene-5-carboxylic acid amide (Compound 22)

Trifluoroacetic acid (3 mL) was added to a solution of compound 47 (68.3 mg, 0.16 mmol) in $CH_2Cl_2$ (3.0 mL). After 30 min at 23° C., the solution was concentrated in vacuo and purified by silica gel chromatography (5% MeOH in $CH_2Cl_2$) to give 16.6 mg (60%) compound 22 as a yellow solid. mp=275° C. (decomposes); $^1H$ NMR (DMSO-$d_6$) δ 8.08 (s, 1H), 7.95 (d, J=5.9 Hz, 1H), 7.78 (d, J=7.4 Hz, 1H), 7.66 (s, 1H), 7.53 (s, 1H), 7.44 (d, J=7.4 Hz, 1H), 6.08 (d, J=5.9 Hz, 1H); IR (KBrpellet) 3383, 1705, 1658 $cm^{-1}$; HRMS (M+H$^+$): Calcd. for $C_{10}H_8NO_2$: 174.0555; Found 174.0559; Anal. ($C10H_7NO_2 \cdot 0.1H_2O$) C, H, N.

Example 41
5-(t-Butyl)-diphenyl-silanyloxymethyl)isophthalic acid diethyl ester (Compound 51)

A solution of 5-hydroxymethyl-isophthalic acid diethyl ester compound 50 (20.0 g, 79.4 mmol) and imidazole (10.81 g, 158.8 mmol) in DMF (265 mL) was treated with t-butylchlorodiphenyl silane (19.6 mL, 75.4 mmol) at 23° C. This solution was held at 23° C. overnight, then saturated aqueous ammonium chloride (200 mL) and EtOAc (200 mL) were added. The EtOAc layer was washed with additional ammonium chloride solution (100 mL), then washed with brine (100 mL). Evaporation of the organics yielded 39.9 g of product as colorless oil. $^1H$ NMR ($CDCl_3$) δ 8.57 (1H, s), 8.22 (1H, s), 7.70–7.67 (5H, m), 7.46–7.35 (6H, m), 4.84 (2H, s), 4.40 (4H, q, J=7.1), 1.42 (6H, t, J=7.1), 1.12 (9H, s).

Example 42
5-(t-Butyl-diphenyl-silanyloxymethyl)isophthalic acid monomethyl ester (Compound 52)

A solution of compound 51 (39.9 g, 81.3 mmol), in MEOH (1.2 L) was treated with 0.95N aqueous NaOH (83.6 mL, 79.4 mmol) at 23° C. The resulting solution was held at 23° C. for 3 d, then acidified with saturated aqueous citric acid. MeOH was removed by evaporation, and the remaining aqueous solution was cooled to 5° C. and held overnight, upon which precipitation occurred. The precipitated was collected by filtration, washed with ice water (3×50 mL), then dried to yield 31.0 g (87% overall) of compound 52 as a white powder. $^1H$ NMR ($CDCl_3$) δ 8.65 (1H, s), 8.28 (1H, s), 8.25 (1H, s), 7.70–7.67 (4H, m), 7.45–7.36 (6H, m), 4.84 (2H, s), 3.96 (3H, s), 1.12 (9H, s).

Example 43
3-(t-Butyl-diphenyl-silanyloxymethyl)-5-hydroxymethyl-benzoic acid (Compound 53)

A solution of compound 52 (27.2 g, 60.6 mmol) in THF (400 mL) was treated with lithium triethylborohydride (212.0 mL of a 1 M solution in THF, 212.0 mmol) at 23° C., and the resulting solution was held overnight at 23° C., then quenched with a saturated aqueous citric acid solution (200 mL). This mixture was evaporated to dryness, then re-dissolved in EtOAc (500 mL), and washed with brine (3×100 mL). Evaporation of the organic layer yielded 26.8 g of alcohol as a white powder. $^1H$ NMR ($CDCl_3$) δ 8.01 (2H, s), 7.74–7.68 (4H, m), 7.59 (1H, s), 7.44–7.36 (6H, m), 4.82 (2H, s), 4.77 (2H, s), 1.12 (9H, s). MS (FAB) 553 (MCS$^+$).

Example 44
3-(t-Butyl-diphenyl-silanyloxymethyl)-5-(2-ethoxy-carbonyl-vinyl)-benzoic acid (Compound 55)

A mixture of compound 53 (24.8 g, 59.0 mmol,), NMO (10.4 g, 88.5 mmol), and powdered 3A molecular sieves (5 g) in methylene chloride (118 mL) was treated with TPAP (1.04 g, 2.95 mmol,), then stirred vigorously for 2 h at 23° C. The mixture was then treated with saturated aqueous citric acid (100 mL) and EtOAc (500 mL). The organic layer was washed with brine (200 mL) and then evaporated to yield 3-(t-butyl-diphenylsilanyloxymethyl)-5-formyl-benzoic acid compound 54 (21.0 g). $^1H$ NMR ($CDCl_3$) δ 10.08 (1H, s), 8.49 (1H, s), 8.33 (1H, s), 8.09 (1H, s), 7.73–7.66 (4H, m), 7.44–7.36 (6H, m), 4.87 (2H, s), 1.13 (9H, s).

A solution of triethyl phosphonoacetate (58.0 mL, 295.0 mmol) in DMF (300 mL) was cooled to 0° C. and treated with sodium hydride (11.8 g of 60% in mineral oil, 295 mmol). This mixture was held at 0° C. for 30 min, then treated with a solution of compound 54 (21.0 g, 50.2 mmol) in DMF (300 mL) at 0° C. This mixture was allowed to warm to 23° C. over a period of 3 h, then held at 23° C. overnight. The mixture was then acidified with saturated aqueous citric acid (500 mL), then extracted with EtOAc (1 L). The organic layer was washed with brine (3×150 mL), then evaporated to yield 54.0 g of a dark oil. Purification by silica gel chromatography (EtOAc-hexanes elutant) yielded 14.8 g (51% overall) of a colorless oil that solidified upon standing at 23° C. $^1H$ NMR ($CDCl_3$) δ 8.17 (1H, s), 8.06 (1H, s), 7.74–7.67 (6H, m), 7.45–7.39 (6H, m), 6.50 (1 H, d, J=16.2), 4.82 (2H, s), 4.29 (2H, q, J=7.0), 1.36 (3H, t, J=7.0), 1.12 (9H, s).

Example 45
3-Bromomethyl-5-(2-ethoxycarbonyl-vinyl)benzoic acid (Compound 57)

A solution of compound 55 (5.0 g, 10.2 mmol) in THF (34 mL) was treated with TBAF (15.3 mL of a 1 M solution in THF, 15.3 mmol), and allowed to stand at 23° C. overnight. The solution was then treated with a saturated aqueous sodium bicarbonate solution, and extracted with diethyl ether (2×20 mL). The aqueous layer was acidified with a saturated citric acid solution (50 mL), then extracted with EtOAc (2×50 mL). Evaporation of the organics yielded 2.6 g of a white powder compound 56. $^1H$ NMR ($CDCl_3$) δ 8.18 (1H, s), 8.10 (1H, s), 7.79 (1H, s), 7.72 (1H, d, J=16.0), 6.55 (1H, d, J=16.0), 4.81 (2H, s), 4.28 (2H, q, J=7.0), 1.35 (3H, t, J=7.0).

This material (compound 56) was dissolved in methylene chloride (50 mL), and treated with phosphorous tribromide (2.91 mL, 30.6 mmol) and held at 23° C. overnight. The solution was then treated with saturated aqueous sodium bicarbonate (50 mL), and extracted with diethyl ether (2×30 mL). The aqueous layer was acidified with saturated aqueous citric acid (50 mL), then extracted with citric acid (3×30 ml). Evaporation of the organic layer yielded 2.2 g (70% overall) of compound 57 as a white powder. $^1H$ NMR ($CDCl_3$) δ 8.20 (1H, s), 8.13 (1H, s), 7.77 (1H, s), 7.71 (1H, d, J=16.2), 6.56 (1H, d, J=16.2), 4.54 (2H, s), 4.29 (2H, q, J=7.0), 1.35 (3H, t, J=7.0).

Example 46
3-(3-Carbamoyl-5-hydroxymethyl-phenyl)-acrylic acid ethyl ester (Compound 13)

FMOC-Rink polystyrene resin (0.50 g, 0.16 mmol) in a shaking vessel was treated with a 1:1 mixture of piperidine and DMF (15 mL), and shaken for 30 min. The resin was washed with DMF (3×15 mL) and $CH_2Cl_2$ (3×15 mL). Acid compound 55 (122 mg, 0.25 mmol,) in DMF (10 mL) was added to the resin, followed by DIEA (0.09 mL, 0.50 mmol) and HATU (95 mg, 0.25 mmol,). The mixture was shaken 1 h, then drained and washed with DMF (3×15 mL) and $CH_2Cl_2$ (3×15 mL). TBAF (0.8 mL of 1 M solution in THF, 0.80 mmol) and THF (10 mL) was added to the resin and shaken for 4 h. The vessel was drained and washed with THF (3×15 mL), MeOH (3×15 mL), H$_2$O (3×15 mL), MeOH (3×15 mL), and CH$_2$Cl$_2$ (3×15 mL). The linker was cleaved with 95:5 TFA-H$_2$O. (20 mL). Evaporation of the solvent followed by purification of the residue on silica gel (EtOAc elutant) yielded 37 mg (90%) of compound 13. $^1$H NMR (CD$_3$OD) δ8.04 (1H, s), 7.94 (1H, s), 7.80 (1H, s), 7.77 (1H, d, J=16.2), 6.66 (1H, d, J=16.1), 4.72 (2H, s), 4.29 (2H, q, J=7.0) 1.36 (3H, t, J=7.0). MS (FAB) 250 (MH$^+$) 272 (MNa$^+$).

Example 47

Resin 58 (functionalized with 3-Bromomethyl-5-(2-ethoxycarbonyl-vinyl)-benzoic acid compound 57)

FMOC-Rink amide polystyrene resin (3.00 g, 1.97 mmol) was treated with a 1:1 mixture of piperidine and DMF (30 mL), and shaken 30 min. The vessel was drained and the resin was washed with DMF (3×25 mL), then CH$_2$Cl$_2$ (3×25 mL). In another flask, compound 57 (0.93 g, 2.96 mmol) and HOBT (0.40 g, 2.96 mmol) in CH$_2$Cl$_2$ (30 mL) was treated with DIC (0.93 mL, 5.91 mmol) and held at 23° C. for 45 min. This solution was then added to the resin and shaken for 6 h. The vessel was drained and the resin was washed with CH$_2$Cl$_2$ (3×25 mL), MeOH (3×25 mL), then CH$_2$Cl$_2$ (3×25 mL). The resin 58 was dried under vacuum and stored in a dessicator.

Example 48

3-[3-Carbamoyl-5-(5-pyridin-2-yl-[1,3,4]oxaldiazol-2-ylsulfanylmethyl-phenyl]-acrylic acid ethyl ester (Compound 25)

Resin 58 (100 mg, 0.063 mmol) in DMF (1 mL) and DIEA (0.11 mL, 0.63 mmol) in a screw-top vial was treated with 2-(2-pyridyl)-5-thiol-1,3,4-oxadiazole (50 mg, 0.28 mmol) and heated at 70° C. overnight. The resin was then transferred to a fritted vessel and washed with DMF (3×10 mL), MeOH (3×10 mL), and CH$_2$Cl$_2$ (3×10 ml). The resin was treated with 95:5 TFA-CH$_2$Cl$_2$ (10 mL), shaken 1 h, and filtered, and the filtrate evaporated. The residue was treated with 10% Et$_3$N-MeOH (3 mL), then evaporated again. The resulting material was purified by silica gel chromatography (EtOAc elutant) to yield 10 mg (38%) of compound 25. $^1$H NMR (CDCl$_3$) δ 8.75 (1H, d, J=4.0), 8.18 (1H, d, J=7.7), 8.04–7.88 (3H, m), 7.80 (1H, s), 7.65 (1H, d, J=16.2), 7.51–7.47 (1H, m), 6.51 (1H, d, J=16.2), 6.40 (1H, br s), 5.70 (1H, br s), 4.54 (2H, s), 4.25 (2H, q, J=7.0), 1.32 (3 H, t, J=7.0). MS (FAB) 411 (MH$^+$),433 (MNa$^+$).

Example 49

3-[3-Carbamoyl-5-(4-pyridin-2-yl-piperizin-1-methyl)-phenyl]-acrylic acid ethyl ester (Compound 26)

The title compound was prepared with 1-(2-pyridyl) piperazine using conditions described for the synthesis of compound 25, to yield 12 mg (48%) of compound 26. $^1$H NMR (CDCl$_3$) δ 8.09–8.07 (1H, m), 7.91 (1H, s), 7.79 (1H, s), 7.64 (1H, d, J=16.0), 7.62 (1H, s), 7.47–7.41 (1H, m), 6.62–6.57 (2H, m), 6.48 (1H, d, J=16.0), 4.21 (2H, q, J=7.0), 3.55 (2H, s), 3.49–3.45 (4H, m), 2.55–2.51 (4H, m), 1.32 (3H, t, J=7.0). MS (FAB) 395 (MH$^+$), 417 (MNa$^+$).

Example 50:

3-(3-{[Benzyl-(2-ethoxycarbonyl-ethyl)-amino]-methyl}-5-carbamoyl-phenyl)-acrylic acid ethylester (Compound 23)

This compound was prepared with N-benzyl-3-aminopropionic acid ethyl ester using conditions described for the synthesis of compound 25, to yield 18 mg (67%) of compound 23. $^1$H NMR (CDCl$_3$) δ 7.95 (1H, s), 7.85 (1H, s), 7.70 (1H, d, J=16.0), 7.50 (1H, s), 7.38–7.20 (5H, m), 6.95 (1H, s), 6.60 (1H, d, J=16.0), 5.70 (1H, s), 4.25 (2H, q, J=7.0), 4.15 (2H, q, J=7.0), 3.75 (2H, s), 3.63 (2H, s), 2.82 (2H, t, J=5.0), 2.55 (2H, t, J=5.0), 1.36 (3 H, t, J=7.0). MS (ES) 439 (MH$^+$), 461 (MNa$^+$).

Example 51

3-{3-Carbamoyl-5-[(ethyl-pyridin-4-yl-methyl-amino)-methyl]-phenyl}-acrylic acid ethyl ester (Compound 27)

This compound was prepared with 4-(ethylaminomethyl) pyridine using conditions described for the synthesis of compound 25, to yield 10 mg (43%) of compound 27. $^1$H NMR (CDCl$_3$) δ 8.75 (2H, d, J=4.0), 8.05 (1H, s), 7.95 (1H, s), 7.75–7.55 (4H, m), 6.50 (1H, d, J=16.0), 4.30 (2H, q, J=7.0), 4.18 (2H, q, J=8.0), 3.95 (2H, s), 3.90 (2H, s), 1.40–1.20 (6H, m). MS (ES) 368 (MH$^+$), 390 (MNa$^+$).

Example 52

4-[3-Carbamoyl-5-(2-ethoxycarbonyl-vinyl)-benzyl]-piperazine-1-carboxylic acid ethyl ester (Compound 28)

This compound was prepared with ethyl-1-piperazine carboxylate using conditions described for the synthesis of compound 25, to yield 15 mg (63%) of compound 28. $^1$H NMR (CDCl$_3$) δ 8.07 (1H, s), 7.90 (1H, s), 7.66 (1H, s), 4.19 (2H, q, J=7.4), 4.14 (2H, s), 4.07 (2H, q, J=7.4), 3.68 (4H, m), 3.55 (4H, m), 1.26 (3H, t, J=7.4), 1.19 (3H, t, J=7.4). MS (ES) 390 (MH$^+$), 412 (MNa$^+$).

Example 53

3-{3-Carbamoyl-5-(4-pyrimidin-2-yl-piperazin-1-ylmethyl)-phenyl}-acrylic acid ethyl ester (Compound 29)

This compound was prepared with 1-(2-pyrimidyl) piperazine using conditions described for the synthesis of compound 25, to yield 15 mg (60%) of compound 29. $^1$H NMR (CDCl$_3$) δ 8.30 (2H, d, J=4.8), 7.88 (1H, s), 7.80 (1H, s), 7.71 (1H, d, J=16.2), 7.70 (1H, s), 6.53 (1H, d, J 16.2), 6.48 (1 H, t, J=4.8), 4.27 (2 H, q, J=7.0), 3.84 (4 H, t, J=5.2), 3.59 (2 H, s), 2.51 (4 H, t, J=4.8), 1.34 (3 H, t, J=7.0). MS (FAB) 396 (MH$^+$), 418 (MNa$^+$).

Example 54

3-{3-Carbamoyl-5-[4-(2-cyano-phenyl)-piperazin-1-ylmethyl]-phenyl}-acrylicacid ethyl ester (Compound 30)

This compound was prepared with 1-(2-cyanophenyl)-piperazine using conditions described for the synthesis of compound 25, to yield 19 mg (73%) of compound 30. $^1$H NMR (CDCl$_3$) δ 7.90 (1H, s), 7.81 (1H, s), 7.70 (1H, d, J=15.8), 7.69 (1H, s), 7.57–7.54 (1H, m), 7.51–7.45 (1H, m), 7.03–6.98 (2H, m), 6.53 (1H, d, J=15.8), 4.27 (2H, q, J=7.4), 3.63 (2H, s), 3.24 (4H, q, J=4.8), 2.68 (4H, q, J=4.8), 1.34 (3H, t, J=7.0). MS (FAB) 419 (MH$^+$), 441 (MNa$^+$).

Synthesis Schemes

The original synthesis of parent compound 1 is outlined in Scheme 1 involving functional group modification of 3-formyl benzoic acid followed by Wittig olefination (Method A). A more versatile route was later devised employing a palladium catalyzed Heck reaction (Heck, R. F. In *Palladium Reagents in Organic Syntheses*, Katritky, A. R., Meth-Cohn, O., Rees C. W., Eds.; Academic Press: London, 1985.) between an acrylate ester and iodobenzamide, compound 32, (Method B). Preparation of the various cinnamyl ester derivatives 3–6 utilizes cinnamic acid derivative, compound 33, as a key intermediate.

Scheme 1[a]

Method A

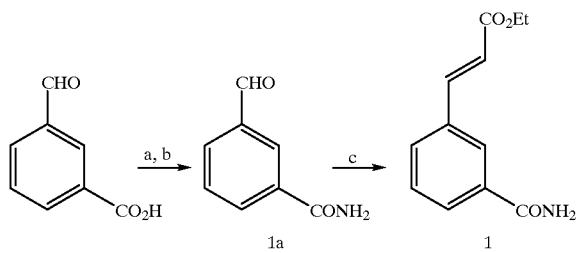

Method B

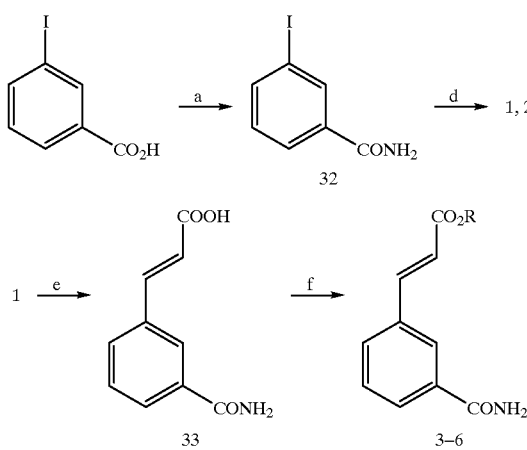

[a] (a) (COCl)$_2$, cat. DMF; (b) NH$_4$OH, THF; (c) Ph$_3$PCH$_2$CO$_2$Et, PhCH$_3$, reflux; (d) CH=CHCO$_2$Me, Pd(OAc)$_2$, Et$_3$N, 100° C.; (e) NaOH/MeOH; (f) EDC, DMF, ROH, Et$_3$N, DMAP Scheme 2 details the straightforward preparation of compounds 7–10 using similar chemistry.

Scheme 2[a]

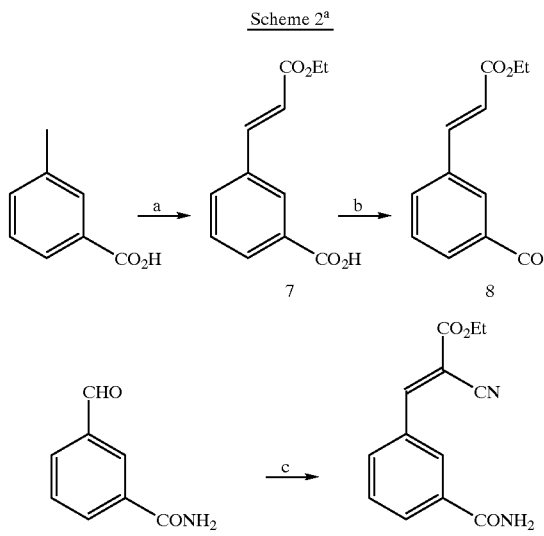

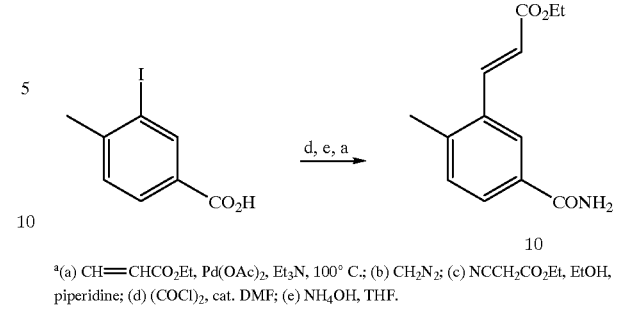

[a] (a) CH=CHCO$_2$Et, Pd(OAc)$_2$, Et$_3$N, 100° C.; (b) CH$_2$N$_2$; (c) NCCH$_2$CO$_2$Et, EtOH, piperidine; (d) (COCl)$_2$, cat. DMF; (e) NH$_4$OH, THF.

The synthesis of 5-substituted compound 11 began with selective reduction of 3,5-dinitroanisole and conversion to iodobenzamide, compound 49, followed by standard Heck coupling as before (Scheme 3).

Scheme 3[a]

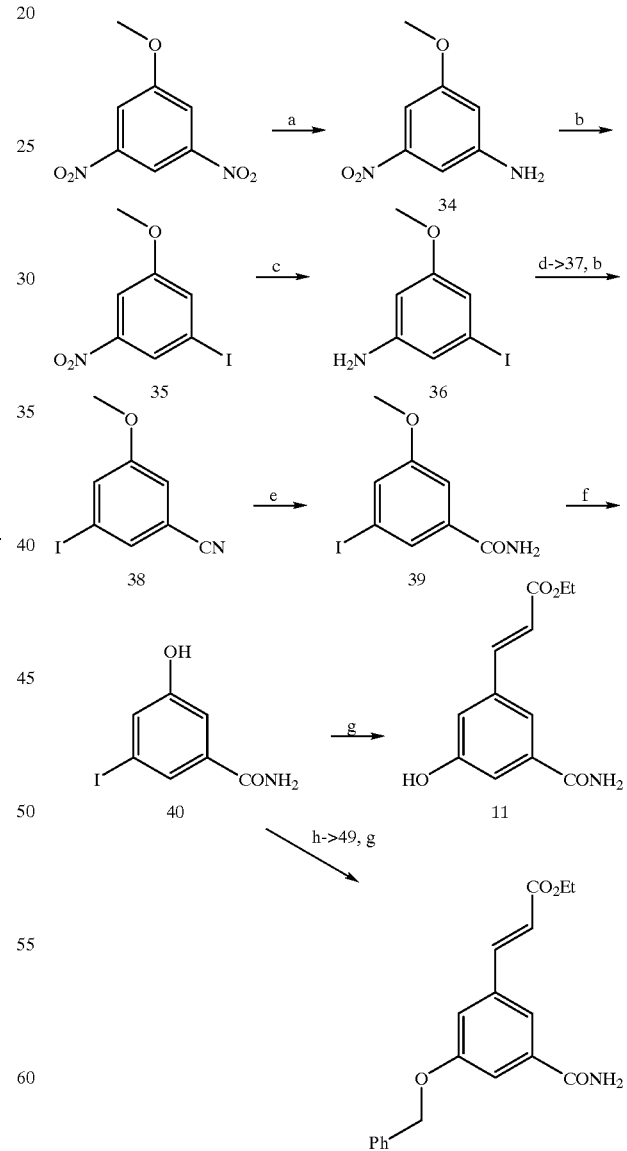

[a] (a) NaSH, MeOH, °C; (b) NaNO$_2$, HCl; KI; (c) Fe$_3$(CO)$_{12}$, EtOH, reflux; (d) Zn(CN)$_2$, Pd(PPh$_3$)$_4$, DMF; (e) H$_2$O$_2$, KOH, H$_2$O; (f) BBr$_3$, CH$_2$Cl$_2$; (g) CH=CHCO$_2$Et, Pd(OAc)$_2$, Et$_3$N, 100° C.; (h) BzBr, K$_2$CO$_3$, DMF Phenol, compound 14, and phenolic ether, compound 15, were prepared from commercially available 3-cyanoanisaldehyde (Scheme 4).

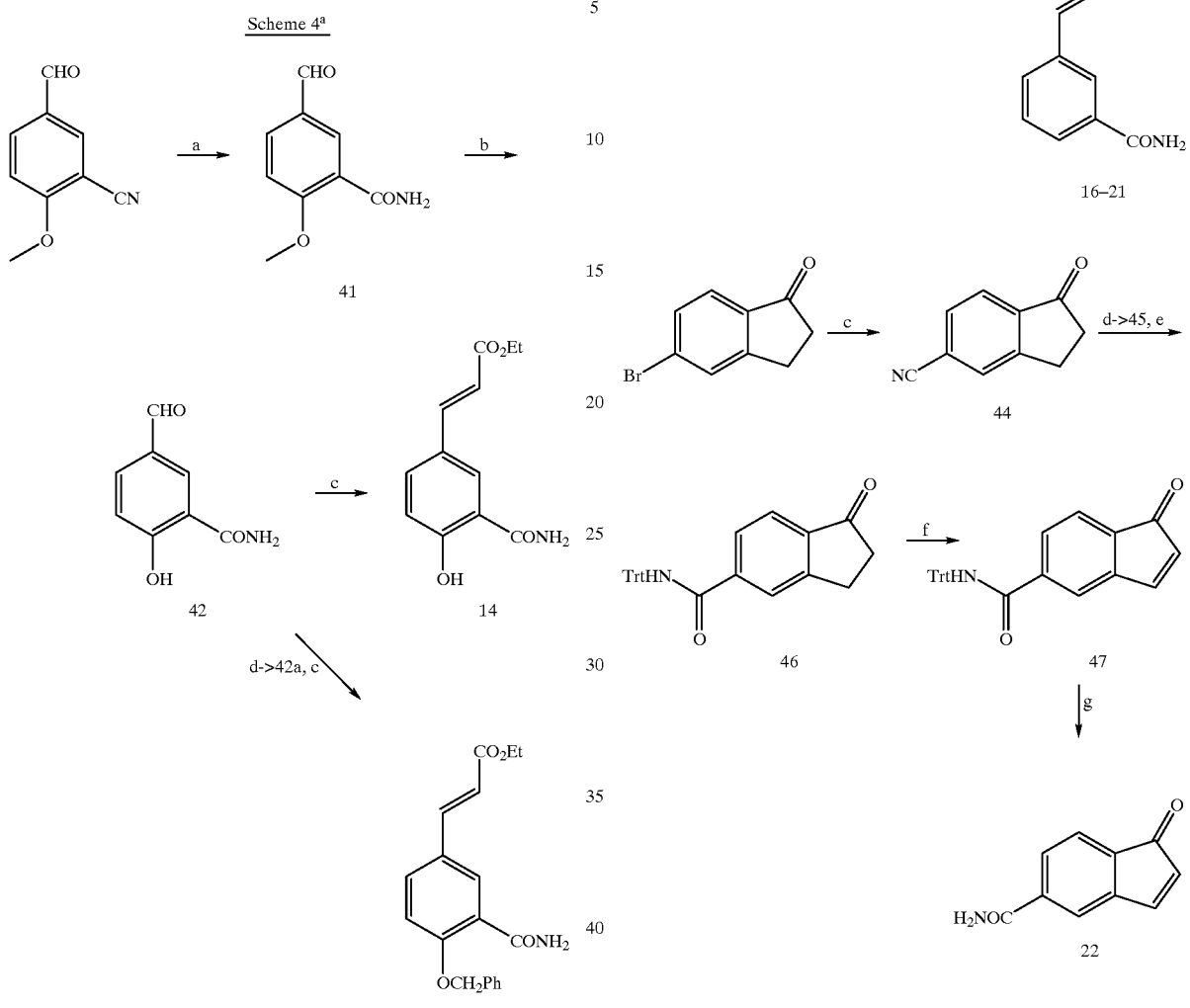

[a] (a) H₂SO₄, 100° C.; (b) BBr₃, CH₂Cl₂; (c) Ph₃P=CHCO₂Et, DMF; (d) BzBr, K₂CO₃, DMF.

The synthesis of α,β-unsaturated ketones, compounds 16–21, began with the preparation of Weinreb amide, compound 43, again via a Heck coupling (Scheme 5).

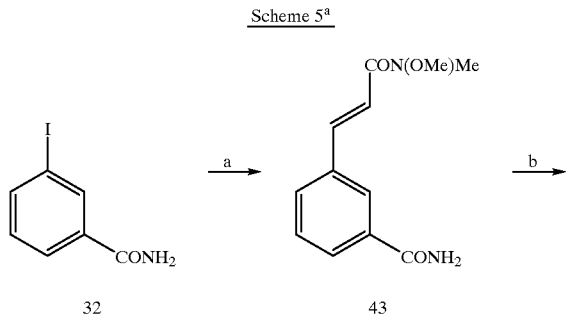

[a] (a) CH=CHCON(OMe)Me, Pd(OAc)₂, Et₃N, 100° C.; (b) RLi, -78° C.; (c) Zn(CN)₂, Pd(PPh₃)₄, DMF; (d) H₂O₂, KOH, H₂O; (e) Ph₃COH, Ac₂O, AcOH, cat. H₂SO₄; (f) NBS, hʋ; then Et₃N; (g) TFA, CH₂Cl₂.

Reaction of the required organolithium species with amide compound 43 afforded ketones in good yield. The organolithium reagents were commercial, or were obtained through metallation of either the corresponding bromide or, in the case of furan, (Sieber, P., Riniker, B. Protection of Carboxamide Functions by the Trityl Residue. Application to Peptide Synthesis *Tet. Lett.* 1991, 32, 6, 739–742.) via direct metallation of the heterocycle. Finally, indenone compound 22 was obtained by palladium catalyzed cyanation of 5-bromoindenone, followed by hydrolysis to the primary amide. Attempted manipulation of the unprotected indenone carboxamide compound 45 led only to decomposition products. Protection of compound 45 as the trityl amide (Dondoni, A., Junquera, F., Merchan, F. L., Merino, P., Tejero, T. *Synthesis* 1994 1450–1456), however, permitted α-bromination with NBS followed by elimination and TFA deprotection to afford the desired indenone compound 22.

The construction of a library of 5-substituted benzamides began with the preparation of the benzylic bromide intermediate compound 57 as outlined in Scheme 6.

Scheme 6[a]
Preparation of Monomer 57 for Parallel Synthesis

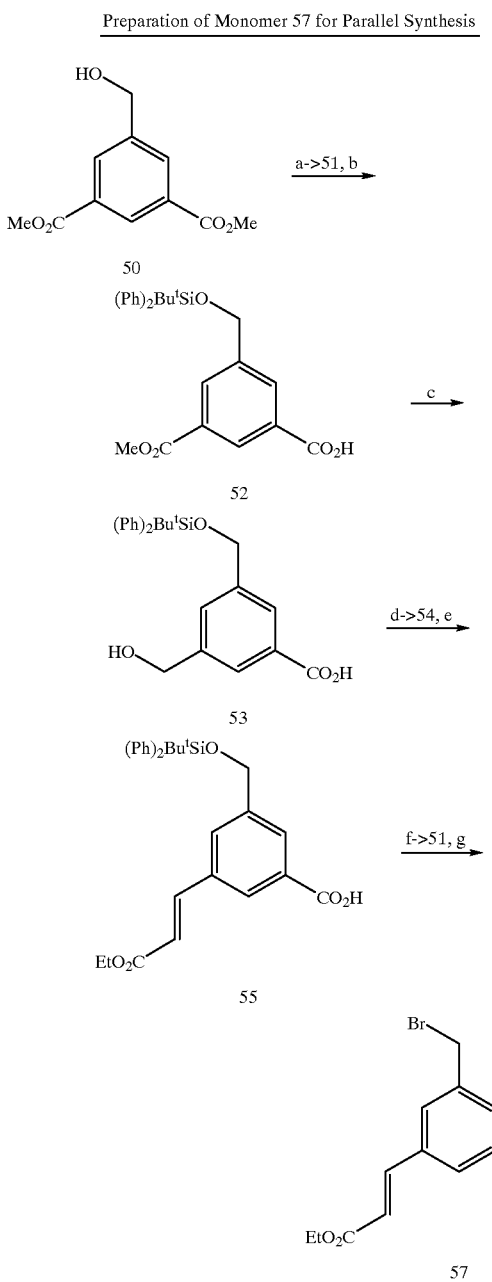

[a] (a) TBDPS—Cl, imidazole, DMF; (b) MeOH, NaOH 1equiv; (c) LiHB(Et₃); (d) TPAP; (e) EtO₂CP(O)(OEt)₂, NaH; (f) TBAF; (g) PBr₃.

Protection of commercially available diethyl-5-(hydroxymethyl)isophthalate compound 50 and selective hydrolysis of one ester gave benzoic acid derivative compound 52. Selective reduction of the ester with Li-triethylborohydride afforded hydroxymethyl acid compound 53. Oxidation to the aldehyde with TPAP followed by Horner-Emmons condensation and silyl deprotection gave penultimate compound 56 in good yield. Lastly, conversion of the hydroxymethyl group to the benzyl bromide with PBr₃ produced key intermediate compound 57 ready for attachment to solid support. Monomer compound 57 was coupled to Rink amide resin (either free resin or Chiron Crowns) using a standard DIC/HOBT coupling procedure (Scheme 7). Nucleophilic displacement of bromide compound 58 in DMF occurred with no indication of Michael addition products. TFA deprotection of coupled products, compound 59, afforded final products of high purity.

Scheme 7[a]
Parallel Synthesis of 5-Substitsted Benzamide on Solid Support

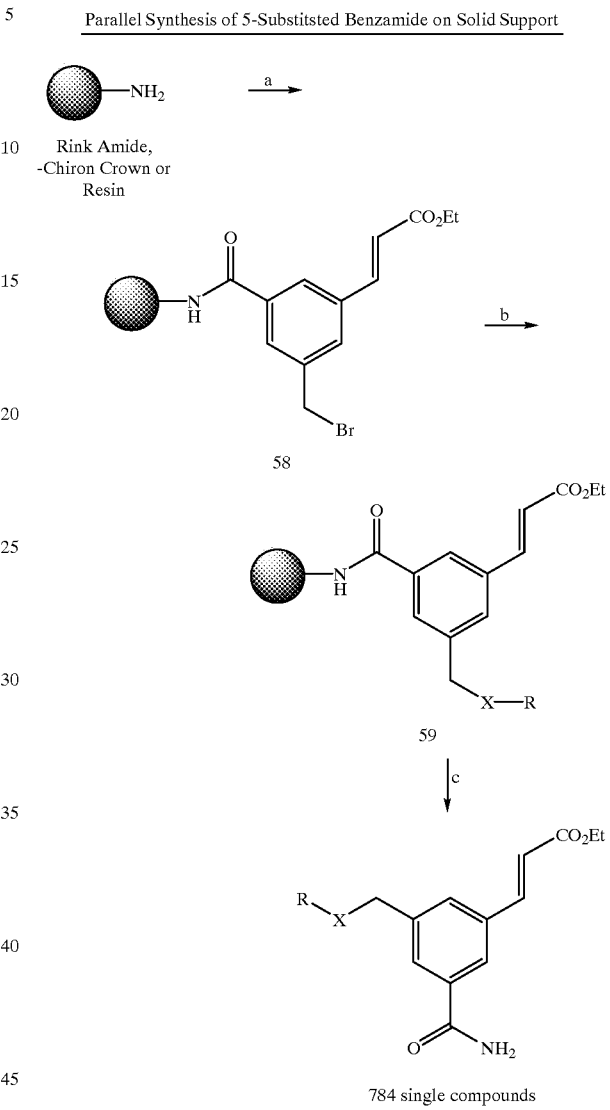

784 single compounds

[a] (a) 57, DIC, HOBt; (b) RR1NH or RSH, DIEA, DMF, 70° C.; (c) TFA.

Solution of the cocrystal structure of this series of inhibitors in complex with the 3CP confirms that they bind essentially as modeled. The α,β-unsaturated ester group suffers irreversible covalent 1,4-addition by the nucleophilic catalytic cysteine on the protein, which is confirmed in the cocrystal structure. Structural feedback facilitated the optimization of compounds attempting to access S2 and S3 subsites of the enzyme. Unfortunately, access to the S2 subsite was not achieved with this class of inhibitors. A related series of unsaturated ketones display potent reversible inhibition, however, they suffer from inactivation by free thiols, and presumably as a result, exhibit no antiviral activity. It has been shown in previous studies that recognition in the S2 pocket can lead to significant enhancements in binding. A parallel synthesis effort on solid phase allowed for the preparation of a large number of benzamide derivatives substituted in the 5-position to access the S3–S4 subsites of the enzyme. These derivatives were confirmed to occupy the S3–S4 pockets through crystallographic analysis; however, only modest improvement in enzyme inactivation were realized. Despite very modest inactivation constants ($K_{obs}/I$), submicromolar antiviral activity was observed with compound 30. It appears from our work and that of others that recognition at S1–S3 subsites and selective irreversible binding is necessary to achieve potent 3CP inactivation.

Results from biological tests on the compounds are described below.

TABLE 1

Substituted Benzamides

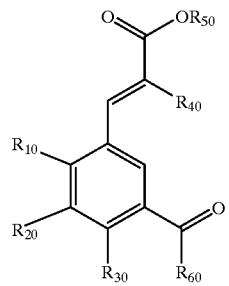

| Cmpd No.[a] | $R_{10}$ | $R_{20}$ | $R_{30}$ | $R_{40}$ | $R_{50}$ | $R_{60}$ | $K_{obs}/[I]$ ($M^{-1}s^{-1}$) or $[K_i$ (mM)][b] | $EC_{50}$ (mM)[b] | $CC_{50}$ (mM)[b] |
|---|---|---|---|---|---|---|---|---|---|
| 1 | H | H | H | H | Et | $NH_2$ | 52 | 15.9 | >320 |
| 2 | H | H | H | H | Me | $NH_2$ | 28 | 150 | >320 |
| 3 | H | H | H | H | $CH_2Ph$ | $NH_2$ | 25 | 5.6 | >100 |
| 4 | H | H | H | H | $CH_2CH_2OH$ | $NH_2$ | 42 | 20 | >320 |
| 5 | H | H | H | H | $CH_2CH_2Ph$ | $NH_2$ | 83 | 100 | >320 |
| 6 | H | H | H | H | $CH_2$(2-pyridyl) | $NH_2$ | 57 | 10 | >320 |
| 7 | H | H | H | H | Et | OH | NI | NT | NT |
| 8 | H | H | H | H | Et | OMe | NI | NT | NT |
| 9 | H | H | H | CN | Et | $NH_2$ | [1.5] | >100 | >100 |
| 10 | Me | H | H | H | Et | $NH_2$ | 10% @ 25 | >100 | >100 |
| 11 | H | OH | H | H | Et | $NH_2$ | 47 | >100 | >100 |
| 12 | H | $OCH_2Ph$ | H | H | Et | $NH_2$ | NI | NT | NT |
| 13 | H | $CH_2OH$ | H | H | Et | $NH_2$ | 54 | >100 | >100 |
| 14 | H | H | OH | H | Et | $NH_2$ | NI | NT | NT |
| 15 | H | H | $OCH_2Ph$ | H | Et | $NH_2$ | 30 | >320 | >320 |

Notes:
[a]Elemental analyses (C,H,N) of all compounds agreed to within +/− 0.4% of theoretical values.
[b]Serotype 14; NI = no inhibition; ND = not determined.

TABLE 2

α, β Unsaturated Keto Benzamides

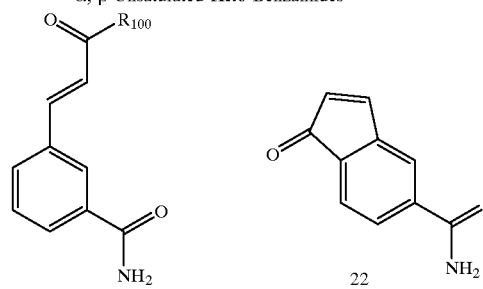

| Cmpd No.[a] | $R^{100}$ | Ki (mM)[b] | DTT inhib.[c] | $EC_{50}$ (mM)[b] | $CC_{50}$ (mM)[b] |
|---|---|---|---|---|---|
| 16 | Me | 25 | yes | 32 | 40 |
| 17 | Ph | 0.40 | yes | 28 | >28 |
| 18 | Ph(4-$NMe_2$) | 9 | yes | >15 | >15 |
| 19 | Ph(4-OMe) | 1.8 | yes | >22 | >22 |
| 20 | 2-pyridyl | 1.8 | yes | >50 | >50 |
| 21 | 2-furyl | 1.9 | yes | >71 | >71 |

TABLE 2-continued

α, β Unsaturated Keto Benzamides

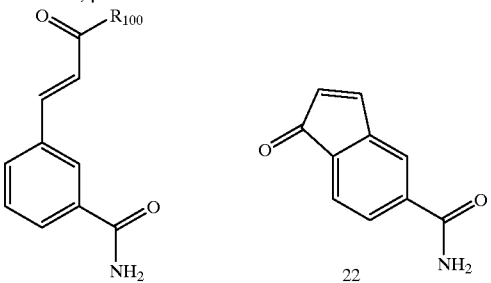

| Cmpd No.[a] | $R^{100}$ | Ki (mM)[b] | DTT inhib.[c] | $EC_{50}$ (mM)[b] | $CC_{50}$ (mM)[b] |
|---|---|---|---|---|---|
| 22 | | 0.12 | yes | >20 | >20 |

Notes:
[a]Elemental analyses (C,H,N) of all compounds agreed to within +/− 0.4% of theoretical values.
[b]Serotype 14; [c]Indicates loss of 3CP inhibitory activity after exposure of compound to 5 mM DTT for 2–3 min at 23° C.

TABLE 3

5-Substituted Benzamides

| Cmpd No.[a] | R₁ | $K_{obs}/[I]$ $(M^{-1}s^{-1})$[b] | $EC_{50}$ $(mM)$[b] | $CC_{50}$ $(mM)$[b] |
|---|---|---|---|---|
| 13 | OH | 54 | >100 | >100 |
| 23 | benzyl-N(Me)-CH₂CO₂Et | 568 | 10.0 | >100 |
| 25 | 2-(2-pyridyl)-5-(methylthio)-1,3,4-oxadiazole | 286 | 5.6 | >100 |
| 26 | 4-methyl-1-(2-pyridyl)piperazine | 269 | 2.5 | >100 |
| 27 | (4-pyridyl)-CH₂-N(Me)(Et) | 96 | 5.8 | >100 |
| 28 | 1-(ethoxycarbonyl)-4-methylpiperazine | 130 | 1.8 | >100 |
| 29 | 4-methyl-1-(2-pyrimidinyl)piperazine | 163 | 1.0 | >100 |
| 30 | 1-(2-cyanophenyl)-4-methylpiperazine | 139 | 0.6 | 79 |

Notes:
[a] HRMS, NMR, and HPLC purity were all consistent with the indicated structures.
[b] Serotype 14.

With the aid of the cocrystal structure of a peptide aldehyde (Webber, S. E., Okano, K., Little, T., Reich, S. H., Xin, Y., Fuhrman, S. A., Matthews, D. A., Love, R. A., Hendrickson, T. F., Patick, A. K., Meador, J. W., Ferre, R. A., Brown, E. L., Ford, C. E., Binford, S. L., Worland, S. T. Tripeptide Aldehyde Inhibitors of Human Rhinovirus 3C Protease: Design, Synthesis, Biological Evaluation, and Cocrystal Structure Solution of P1 Glutamine Isosteric Replacements *J. Med. Chem.* 1998, 41, 2786–2805.) bound to the 3CP, the design of novel nonpeptide inhibitor S was undertaken. Analysis of the 2.3 A crystal structure of the HRV-14 3CP enzyme verified that it is structurally related to the trypsin family of proteases, with a catalytic triad composed of the residues cysteine, histidine, and glutamic acid. (Matthews, D. A., Smith, W. A., Ferre, R. A., Condon, B., Budahazi, G., Sisson, W., Villafranca, J. E., Janson, C. A., McElroy, H. E., Gribskov, C. L., Worland, S. Structure of Human Rhinovirus 3C Protease Reveals a Trypsin-like Polypeptide Fold, RNA-Binding Site, and Means for Cleaving Precursor Polyprotein. *Cell* 1994, 77, 761–771.) Our goal was to ultimately develop orally available 3CP inhibitors, so the design strategy focused on non-peptide motifs, which would be expected to have more favorable pharmacokinetic properties. Initial design was deliberately very simple: positioning an aldehyde group so that it could react with the nucleophilic cysteine and placing a carboxamide group in the S1 recognition pocket. A meta-substituted phenyl ring positioned these two elements with the appropriate distance and relative orientation leading to 3-formyl benzamide as a prototype inhibitor compound 1a:

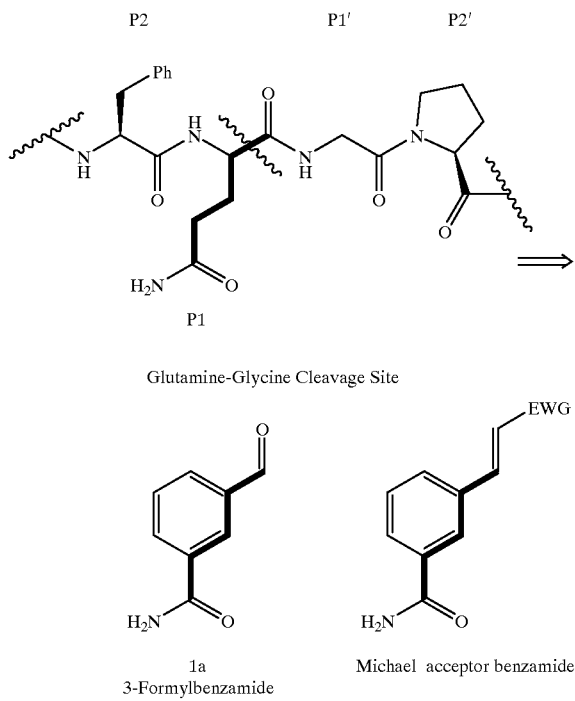

This compound was tested and found to be a very weak inhibitor of the 3CP (Ki=104 μM). In addition to the small size of this inhibitor, its lack of activity, we reasoned, could in part be due to the benzaldehyde carbonyl being considerably less reactive than its α-amino aldehyde counterpart found in potent peptide-based aldehyde inhibitors. (Webber, S. E., Okano, K., Little, T., Reich, S. H., Xin, Y., Fuhrman, S. A., Matthews, D. A., Love, R. A., Hendrickson, T. F., Patick, A. K., Meador, J. W., Ferre, R. A., Brown, E. L., Ford, C. E., Binford, S. L., Worland, S. T. Tripeptide Aldehyde Inhibitors of Human Rhinovirus 3C Protease: Design, Synthesis, Biological Evaluation, and Cocrystal Structure Solution of P1 Glutamine Isosteric Replacements *J. Med. Chem.* 1998, 41, 2786–2805.) Furthermore, the inherent instability of aldehydes made this group undesirable for our purposes. It had been established in our lab (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998, 41, 2806) and others that cysteine proteases in general, and 3CP in particular, are potently inhibited by Michael acceptors when incorporated into a peptidic recognition element. Replacement of the formyl group of inhibitor compound 1a with the α,β-unsaturated ethyl ester led to compound compound 1, which was found to be an irreversible inhibitor with a weak inactivation constant of 52 $s^{-1}M^{-1}$ (Table 1). Interestingly, compound 1 also showed weak but demonstrable antiviral activity ($EC_{50}$) when tested in a cytopathic effect assay (Webber, S. E., Tikhe, J., Worland, S. T., Fuhrman, S. A., Hendrickson, T. F., Matthews, D. A., Love, R. A., Patick, A. K., Meador, J. W., Ferre, R. A., Brown, E. L., DeLisle, D. M., Ford, C. E., Binford, S. L. Design, Synthesis, and Evaluation of Nonpeptidic Inhibitors of Human Rhinovirus 3C Protease. *J. Med. Chem.* 1996, 39, 5072–5082; Webber, S. E., Okano, K., Little, T., Reich, S. H., Xin, Y., Fuhrman, S. A., Matthews, D. A., Love, R. A., Hendrickson, T. F., Patick, A. K., Meador, J. W., Ferre, R. A., Brown, E. L., Ford, C. E., Binford, S. L., Worland, S. T. Tripeptide Aldehyde Inhibitors of Human Rhinovirus 3C Protease: Design, Synthesis, Biological Evaluation, and Cocrystal Structure Solution of P1 Glutamine Isosteric Replacements *J. Med. Chem.* 1998, 41, 2786–2805; Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806; Dragovich, P. S., Webber, S. E, Babine, R. E., Fuhrman, S. A., Patick, A. K., Matthews, D. A., Reich, S. H., Marakovits, J. T., Prins, T. J., Zhou, R., Tikhe, J., Littlefield, E. S., Bleckman, T. M., Wallace, M. W., Little, T. L., Ford, C. E., Wallace, M. B., Meador, III, J. W., Ferre, R., Brown, E. L., Binford, S. L, DeLisle, D. M. and Worland, S. T. Structure-Based Design, Synthesis, and Biological Evaluation of Irreversible Human Rhinovirus 3C Protease Inhibitors. 2. Peptide Structure-Activity Studies. *J. Med. Chem.* 1998, 41, 2819.) and others. (Kaldor, S. W., Hammond, M., Dressman, B. A., Labus, J. M., Chadwell, F. W., Kline, A. D., Heinz, B. A. Glutamine-derived Aldehydes for the Inhibition of Human Rhinovirus 3C Protease. *Bioorg. Med. Chem. Lett.* 1995, 5, 2021–2026. Shepherd, T. A., Cox, G . A., McKinney, E., Tang, J., Wakulchik, M., Zimmerman, R. E., Villarreal, E. C. Small Peptidic Aldehyde Inhibitors of Human Rhinovirus 3C Protease. *Bioorg. Med. Chem. Lett.* 1996, 6, 2893–2896; Malcolm, B. A., Lowe, C., Shechosky, S., McKay, R. T., Yang, C. C., Shah, V. J., Simon, R. J., Vederas, J. C., Santi, D. V. Peptide Aldehyde Inhibitors of Hepatitis A Virus 3C Proteinase. *Biochem.* 1995, 34, 8172–8179; Sham, H. L., Rosenbrook, W., Kati, W., Betebenner, D. A., Wideburg, N. E., Saldivar, A., Plattner, J. J., Norbeck, D. W. Potent inhibitor of the human rhinovirus (ERV) 3C protease containing a backbone modified glutamine. *J. Chem. Soc. Perkin Trans.* 1 1995, 1081–1082; Brill, G. M., Kati, W. M., Montgomery, D., Karwowski, J. P., Humphrey, P. E., Jackson, M., Clement J. J., Kadam, S., Chen, R. H., McAlpine, J. B. Novel Triterpene Sulfates from *Fusarium compactum* Using a Rhinovirus 3C Protease Inhibitor Screen. *J. Antibiotics* 1996, 49, 541–546; Skiles, J. W., McNeil, D. Spiro Indolinone Beta-lactams, Inhibitors of Poliovirus and Rhinovirus 3C-Proteinases. *Tetrahedron Lett.* 1990, 31, 7277–7280; Kadam, S., Poddig, J., Humphrey, P., Karwowski, J., Jackson, M., Tennent, S., Fung, L., Hochlowski, J., Rasmussen, R., McAlpine, J. Citrinin Hydrate and Radicinin: Human Rhinovirus 3C-Protease Inhibitors Discovered in a Target-directed Microbial Screen. *J. Antibiotics* 1994, 47, 836–839; Singh, S. B., Cordingley, M. G., Ball, R. G., Smith, J. L., Dombrowski, A. W., Goetz, M. A. Structure and Stereochemistry of Thysanone: A Novel Human Rhinovirus 3C-Protease Inhibitor from Thysanophora penicilloides. *Tetrahedron Lett.* 1991, 32, 5279–5282; Jungheim, L. N., Cohen, J. D., Johnson, R. B., Villarreal, E. C., Wakulchik, M., Loncharich, R. J., Wang, Q. M. Inhibition of Human Rhinovirus 3C Protease by Homophthalimides. *Bioorg. Med. Chem. Lett.* 1997, 7, 1589–1594; Kong, J. , Venkatraman, S., Furness, K., Nimkar, S., Shepard, T., Wang, Q., Aube', J., Hanzlik, R. P. Synthesis and Evaluation of Peptidyl Michael Acceptors That Inactivate Human Rhinovirus 3C Protease and Inhibit Virus Replication *J. Med. Chem.* 1998 41 2579–2587) employing H1-HeLa cells infected with HRV-14 (Table 1). Furthermore, compound 1 was nontoxic ($CC_{50}$) up to 320 μM.

With this information in hand, additional esters were prepared and tested. It was anticipated that by filling the active site in the prime direction (S1'–S2'), additional affinity might be obtained. The methyl ester compound 2, while showing similarly weak inhibition of the enzyme relative to ethyl ester compound 1, was surprisingly 10-fold less active in the antiviral assay. As shown in Table 1, the ester group, in general, was found to have an unremarkable effect on the potency, with the benzyl ester compound 3 showing the best activity. To determine whether the activity of the parent compound 1 was due to the inherent reactivity of the unsaturated ester, alternative substitutions were examined in the 1-position corresponding to the S1 recognition pocket. A clear preference was observed for the primary carboxamide, consistent with recognition of glutamine in the native substrate peptide. (Webber, S. E., Tikhe, J., Worland, S. T., Fuhrman, S. A., Hendrickson, T. F., Matthews, D. A., Love, R. A., Patick, A. K., Meador, J. W., Ferre, R. A., Brown, E. L., DeLisle, D. M., Ford, C. E., Binford, S. L. Design, Synthesis, and Evaluation of Nonpeptidic Inhibitors of Human Rhinovirus 3C Protease. *J. Med. Chem.* 1996, 39, 5072–5082.) Increased activation of the Michael acceptor toward nucleophilic addition, by alpha cyano substitution, led to a modest but reversible inhibitor, compound 9. Various unsaturated imides, also expected to be more reactive than an unsaturated ester, were poor inhibitors. Exploration of α,β-unsaturated ketones led to some interesting findings. A simple methyl ketone showed only modest, but again, reversible inhibition. However, phenyl ketone compound 17 was considerably more potent against the 3CP. When tested in the antiviral assay, ketones in general had greater toxicity (lower $CC_{50}$) and no measurable antiviral effect. Upon incubation with DTT, the α,β-unsaturated ketones were completely inactivated, suggesting that their lack of antiviral activity may be due to interaction with endogenous thiols in cells (glutathione). (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, J.E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806.) Electron-donating substituents at the 4-position of the phenyl ketone (4-$Me_2N$—, 4-MeO—), were expected to make the ketones less reactive, however, no effect on their inactivation with DTT was observed. Similarly, heterocyclic ketones (2-pyridyl, 2-furyl) maintained their reactivity with DTT. In an attempt to make the inhibitors more compact, an indenone scaffold was designed. Bicyclic indenone compound 22 was the most potent of the ketones; however, it too was inactivated by DTT and had no antiviral activity. It became clear that while small, nonpeptidic α,β-unsaturated ketones such as compound 22 afforded potent reversible inhibition of 3CP, this increased reactivity was incompatible with the more complex cellular milieu present in the cytopathic effect assay.

One of the more soluble unsaturated ester inhibitors, hydroxyethyl ester compound 4, was successfully cocrystallized with the 3CP and a 1.9 A crystal structure was solved. The bound conformation was similar to that of the original model in terms of the phenyl (Ph) core and 3-carboxamide. Interestingly, the orientation of the Michael ester adduct observed in the crystal structure was opposite of that predicted based on modeling studies. That is, the carboethoxy group was rotated away from the 3-carboxamide group in the crystal structure, whereas the modeled compound has the carboethoxy group oriented towards the 3-carboxamide function. This is consistent with the good hydrogen bond (2.98 A) observed between the ester carbonyl and Cys-147 NH, which may activate the ester toward 1,4 addition in the transition state and also appears to be a good interaction in the final complex. In addition, this orientation was subsequently observed in the peptide based Michael acceptors as well. (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806.) Other key interactions between the protein and inhibitor were also observed. The 3-carboxamide is found to make three hydrogen bonds to His161 and Thr 142. The hydrogen bond from the amide NH to the Thr142 carbonyl is slightly longer (3.12 A) and in a less optimal orientation than that observed with peptide based Michael acceptors. (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J.E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med.*

Chem. 1998,41, 2806.) While the carboxamide is 23 degrees out of the aromatic plane, apparently to secure these hydrogen bonds, further rotation out of plane would be required to more closely mimic the hydrogen bonds observed in the P1 glutamine of peptidic inhibitors, with an associated energetic penalty. This molecular recognition explains the specificity for the primary carboxamide over the other groups tested in this position and is consistent with the binding interactions observed with other inhibitors. (Webber, S. E., Tikhe, J., Worland, S. T., Fuhrman, S. A., Hendrickson, T. F., Matthews, D. A., Love, R. A., Patick, A. K., Meador, J. W., Ferre, R. A., Brown, E. L., DeLisle, D. M., Ford, C. E., Binford, S. L. Design, Synthesis, and Evaluation of Non-peptidic Inhibitors of Human Rhinovirus 3C Protease. *J. Med. Chem.* 1996, 39, 5072–5082; Webber, S. E., Okano, K., Little, T., Reich, S. H., Xin, Y., Fuhrman, S. A., Matthews, D. A., Love, R. A., Hendrickson, T. F., Patick, A. K., Meador, J. W., Ferre, R. A., Brown, E. L., Ford, C. E., Binford, S. L., Worland, S. T. Tripeptide Aldehyde Inhibitors of Human Rhinovirus 3C Protease: Design, Synthesis, Biological Evaluation, and Cocrystal Structure Solution of P1 Glutamine Isosteric Replacements *J. Med. Chem.* 1998, 41, 2786–2805; Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J. E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806.) Prior to solution of the cocrystal structure of the benzamide core, we began to explore additional substituents on the phenyl ring to increase affinity. We reasoned that substitution from the 6-position might allow access to the S2 subsite, which was unoccupied, and based on other classes of 3CP compound should improve binding significantly. 4-Methyl, compound 10, however, proved to be less active than the parent unsubstituted compound 1. In retrospect, the ortho-methyl substitution in compound 10 would be expected to prevent the favorable orientation of the Michael acceptor away from the carboxamide as observed in the cocrystal structure of compound 1. Substitution of the Michael acceptor in either the α or β position by a methyl group resulted in complete loss of activity (data not shown). Finally, substitution off the 6-position also resulted in loss of activity.

Analysis of the cocrystal structure of compound 1 indicated that substitution at the 5-position looked particularly promising. The aryl-H vector in the 5-position was directed along the β-sheet toward the S3–S4 pockets and, furthermore, with the appropriate substitution, it appeared that the S2 pocket might be accessible. The phenol compound 11 had comparable activity to that of compound 1, yet the corresponding phenol ethers tested showed a universal lack of activity e.g. compound 12. Hydroxymethylene compound compound 13, however, was found to retain all of the potency of the unsubstituted parent compound 1.

With the tolerance for a hydroxymethyl group at the 5-position observed in compound 13 along with cocrystal structure information, a parallel synthesis approach was undertaken to explore substitution at this position. Using the primary carboxamide group as a handle for attachment to solid support, it was felt that derivatives could be readily accessed through nucleophilic substitution of the corresponding bromomethyl compound.

A search of the Available Chemicals Directory (ACD) for primary amines and mercaptans suitable for synthesis yielded 3087 compounds. A structure-based computational approach was used to rank and select a subset of molecules from the total number that could be synthesized. From the precursor fragments, a virtual library of 5-substituted benzamides was created. This library of 3 D structures was then run through a partially fixed docking procedure, where the benzamide "core" of the molecule was kept fixed to its position as observed in the cocrystal structure, and the remaining atoms were adjusted to find their optimal position in the active site. Once these molecules were docked, they were analyzed and ranked by low energy interactions with the protein, number of additional protein-ligand hydrogen bonds made, and the degree to which they filled the S2, S3 and/or the S4 pocket. The best candidate compounds from this screening and ranking procedure were then selected for synthesis. Of the 784 compounds prepared and tested, about 30 having greater than 80% inhibition of 3CP at 20$\mu$ were selected for resynthesis and full characterization. An internal control compound was used on all plates that produced approximately 25% inhibition at 10 $\mu$M under identical conditions (10 minute preincubation (Dragovich, P. S., Webber, S. E, Babine, R. E., Fuhrman, S. A., Patick, A. K., Matthews, D. A., Lee, C. A., Reich, S. H., Prins, T. J., Marakovits, J. T., Littlefield, E. S., Zhou, R., Tikhe, J., Ford, C. E., Wallace, M. B., Meador, III, J. W., Ferre, R., Brown, E. L., Binford, S. L, Harr, , J.E. V., DeLisle, D. M. and Worland, S. T. Structure-Based Design, Synthesis, and Biological Evaluation of Irreversible Human Rhinovirus 3C Protease Inhibitors. 1. Michael Acceptor Structure-Activity Studies *J. Med. Chem.* 1998,41, 2806.)) As shown in Table 3, a clear preference for branched aminomethylene groups was observed. The rates of inactivation ($K_{obs}$/I), which are modest, do not correlate with the antiviral potency. In fact, for the most potent compound, compound 30, the antiviral $EC_{50}$ of 600 nM is exceptional given the modest $K_{obs}$/I. This lack of a correlation between the rate of inactivation and the antiviral activity prompted us to investigate whether the antiviral effect of these compounds was in fact due to inhibition of the 3CP. Examination of proteolytic processing by 3CP in the cytopathic effect assay using polyacrylamide gel electrophoresis with compound 1 clearly showed a dose-dependent reduction in proteolytic fragments consistent with inhibition of the 3CP. To determine the nature of the binding interactions with the more highly substituted derivatives, a cocrystal structure was solved of compound 26 bound to 3CP. In this instance, a significant change in protein conformation was observed, which is very likely a result of crystal packing forces. The unit cell and space group of this complex was unique and has never been observed in over 30 3CP cocrystal structures. However, the benzamide core of compound 26 binds essentially in the same space and orientation as the unsubstituted compound 4. The piperizine ring lays directly over the backbone of β-sheet with the pyridine ring buried deeply into a larger rearranged P4 subsite. While the pyridine ring is largely buried in the protein, the energetic cost of adopting this new protein conformation is unclear.

While the invention has been illustrated with reference to preferred features and embodiments, appropriate modifications will become apparent to artisans through routine practice of the invention. Accordingly, the invention is intended not to be limited by the foregoing detailed description, but to be defined by the appended claims and their equivalents.

What is claimed is:

1. A compound of the formula

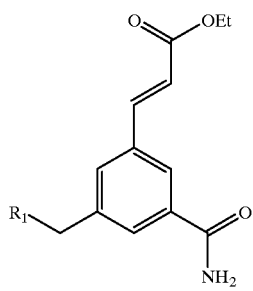

wherein $R_1$ is:

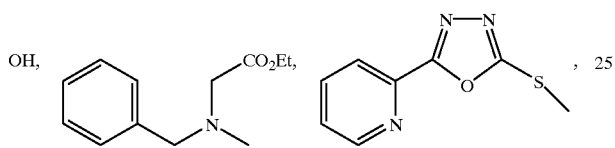

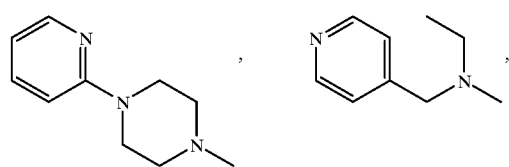

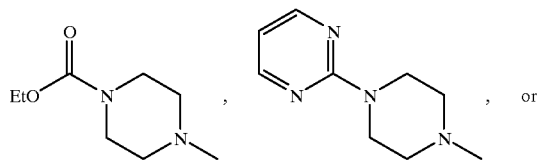

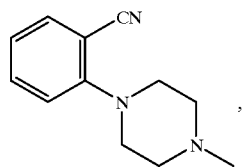

or a pharmaceutically acceptable salt, solvate, prodrug, or pharmaceutically active metabolite thereof.

2. A compound of the formula

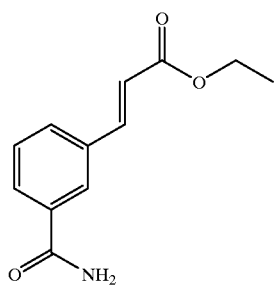

or a pharmaceutically acceptable salt, solvate, prodrug, or pharmaceutically active metabolite thereof.

3. A compound of the formula

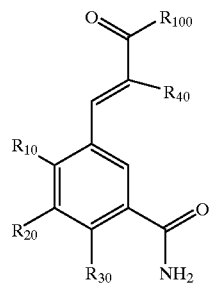

wherein:
$R_{10}$ is H or $CH_3$;
$R_{20}$ is H, OH, $CH_2OH$, or $OCH_2Ph$;
$R_{30}$ is H, OH, or $OCH_2Ph$;
$R_{40}$ is H or CN; and
$R_{50}$ is $CH_2CH_3$, $CH_3$, $CH_2Ph$, $CH_2CH_2Ph$, $CH_2CH_2OH$, or $CH_2$(2-pyridyl);

or a pharmaceutically acceptable salt, solvate, prodrug, or pharmaceutically active metabolite thereof.

4. A compound of the formula

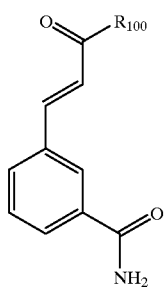

wherein $R_{100}$ is $CH_3$, phenyl, Ph(4-$NCH_3$), Ph(4-$OCH_3$), 2-pyridyl, or 2-furyl; or a pharmaceutically acceptable salt, solvate, prodrug, or pharmaceutically active metabolite thereof.

* * * * *